US011639938B2

(12) United States Patent
Bergo

(10) Patent No.: US 11,639,938 B2
(45) Date of Patent: May 2, 2023

(54) MULTIPLEXED BEAD-BASED ANALYTICAL ASSAYS

(71) Applicant: Adeptrix Corp., Beverly, MA (US)

(72) Inventor: Vladislav B. Bergo, Boston, MA (US)

(73) Assignee: ADEPTRIX CORP., Beverly, MA (US)

( * ) Notice: Subject to any disclaimer, the term of this patent is extended or adjusted under 35 U.S.C. 154(b) by 340 days.

(21) Appl. No.: 16/932,732

(22) Filed: Jul. 18, 2020

(65) Prior Publication Data

US 2021/0018513 A1 Jan. 21, 2021

Related U.S. Application Data

(60) Provisional application No. 62/876,060, filed on Jul. 19, 2019.

(51) Int. Cl.
*G01N 33/68* (2006.01)
*G01N 33/543* (2006.01)

(52) U.S. Cl.
CPC ... *G01N 33/6848* (2013.01); *G01N 33/54313* (2013.01)

(58) Field of Classification Search
CPC ............. G01N 33/6848; G01N 33/54313
See application file for complete search history.

(56) References Cited

U.S. PATENT DOCUMENTS

| 7,846,748 | B2 | 12/2010 | Borchers | |
|---|---|---|---|---|
| 9,618,520 | B2 | 4/2017 | Bergo | |
| 10,101,336 | B2 | 10/2018 | Bergo | |
| 10,451,631 | B2 | 10/2019 | Bergo | |
| 11,131,674 | B2 | 9/2021 | Bergo | |
| 2009/0270278 | A1 | 10/2009 | Lim et al. | |
| 2009/0286258 | A1* | 11/2009 | Kaur | G01N 33/6854 435/7.1 |
| 2010/0256015 | A1 | 10/2010 | Lim et al. | |
| 2010/0317542 | A1 | 12/2010 | Lim et al. | |
| 2012/0077688 | A1 | 3/2012 | Bergo et al. | |
| 2012/0202709 | A1* | 8/2012 | Bergo | B01J 19/0046 506/23 |
| 2014/0235471 | A1 | 8/2014 | Bergo et al. | |
| 2014/0323330 | A1 | 10/2014 | Bergo | |
| 2015/0253341 | A1* | 9/2015 | McAvoy | G01N 33/6848 435/7.1 |

(Continued)

FOREIGN PATENT DOCUMENTS

WO 2021016138 A1 1/2021

OTHER PUBLICATIONS

Hamza et al., "Affinity-Bead Assisted Mass Spectrometry (AffiBAMS): A Multiplexed Microarray Platform for Targeted Proteomics," International Journal of Molecular Sciences, 21(6): 1-36 (2020).

(Continued)

*Primary Examiner* — Jennifer Wecker
*Assistant Examiner* — Oyeleye Alexander Alabi
(74) *Attorney, Agent, or Firm* — Kriegsman & Kriegsman

(57) ABSTRACT

Bead-based analytical assays suitable for detecting changes in the abundance of target analytes in biological samples are disclosed. In an embodiment, an assay involves incubating a sample with one or several beads that are capable of binding several distinct analytes in an amount sufficient for detection by mass spectrometry from a single bead.

19 Claims, 3 Drawing Sheets

Specification includes a Sequence Listing.

(56) References Cited

U.S. PATENT DOCUMENTS

| 2016/0008785 A1 | 1/2016 | Bergo |
| 2017/0176453 A1 | 6/2017 | Bergo |
| 2017/0219601 A1 | 8/2017 | Bergo |
| 2019/0004038 A1 | 1/2019 | Bergo |
| 2019/0072546 A1 | 3/2019 | Bergo |
| 2021/0190773 A1 | 6/2021 | Bergo |
| 2021/0389333 A1 | 12/2021 | Bergo |

OTHER PUBLICATIONS

International Search Report dated Nov. 25, 2020, for PCT Application No. PCT/US20/42689.
Written Opinion dated Nov. 25, 2020, for PCT Application No. PCT/US20/42689.
Hayworth et al., "Calculate the Number of Immobilized Proteins per Bead of Agarose Affinity Supports: A consideration of relative sizes and dimensions of agarose resin beads, antibodies, proteins, chemical modification groups, and affinity ligands," ThermoFisher Scientific Inc., Watham, MA (2014).

\* cited by examiner

MULTIPLEXED BEAD-BASED ANALYTICAL ASSAYS

CROSS-REFERENCE TO RELATED APPLICATIONS

The present application claims the benefit under 35 U.S.C. 119(e) of U.S. Provisional Patent Application No. 62/876,060, inventor Vladislav B. Bergo, filed Jul. 19, 2019, the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Jul. 15, 2020, is named 84233A_SL.txt and is 2,245 bytes in size.

FIELD

The embodiments disclosed herein relate generally to bead-based assays and more specifically to measuring analytes in biological samples using bead-based assays. The embodiments disclosed herein also relate to proteomics, protein quantification, post-translational modifications of proteins, affinity separations, microarrays and mass spectrometry.

BACKGROUND

Detection, identification and quantification of multiple analytes in biological samples is an important area of basic and applied biology. In many applications, the analytes are proteins and/or protein fragments, such as proteolytic peptides produced by enzymatic digestion of precursor proteins. Mass spectrometry (MS) is the key analytical platform for quantitative analysis of proteins and peptides. MS-dependent protein quantification methods can be classified as either label-free or label-based.

Recently there has been considerable progress in the MS-based quantification methods that utilize detection from individual beads or microspheres. One example of such approach, termed "immuno-MALDI" or "iMALDI" is described in the U.S. Pat. No. 7,846,748 and several publications. The iMALDI approach is generally limited to detecting a single analyte. On the other hand, recent U.S. Pat. No. 9,618,520 and U.S. patent application Ser. No. 13/369,939, Publication No. US 2012-0202709 A1 describe various quantitative bead-based methods, which are multiplexed, that is capable of measuring multiple distinct analytes.

While analytical assays utilizing single beads can be readily adapted for use with label-based quantification methods, such as tandem mass tags (TMT) and Stable Isotope Labeling by Amino acids in Cell culture (SILAC), developing label-free assays is more difficult. The challenges include optimizing the analyte binding capacity of individual beads and of the entire bead array, creating conditions that enable depletion of one or more analytes from a sample and detecting the bead-captured analytes using MS.

Accordingly, there is still a need for methods and compositions that will enable analysis of proteins and peptides by MS in a bead array format.

SUMMARY

In one aspect, the present specification describes methods of preparing a sample for analysis by MS. Some of the described methods include depleting one or multiple analytes from the sample by incubating the sample with a bead array.

In another aspect, the present specification describes a bead array, in which individual reactive sites contain at least two distinct capture agents that are present in a specific ratio. A single reactive site of such bead array is capable of binding at least two distinct analytes from a sample.

In yet another aspect, the present specification describes a method of measuring abundance of an analyte in a sample. The method includes the step of binding at least two distinct analytes from the sample to a single reactive site of a bead array, such that one of the analytes becomes substantially depleted from the sample while a certain amount of the other analyte remains in the sample. The bead-captured analytes are subsequently measured by MS from individual reactive sites of the bead array.

In yet another aspect, the present specification describes methods of preparing a bead array for analysis by MS. Some of the described methods involve the step of continuously adding a solution that contains MS matrix to a liquid-filled microwell, such that a rate, at which the matrix solution is being added to the microwell, is substantially equivalent to a rate, at which the solvent of the matrix solution is escaping from the microwell via evaporation. The described methods enable adding the matrix solution to a liquid-filled microwell without splattering or spilling.

In yet another aspect, the present specification describes a microarray, in which spots that contain or are suspected of containing biomolecules are visibly distinct from spots that are devoid of biomolecules. The latter spots may form rows and/or columns, which are located on a periphery of the microarray or separate distinct regions within the microarray. The visibly distinct appearance of the spots that are devoid of biomolecules is used to identify such spots and exclude them from the microarray analysis.

In yet another aspect, the present specification describes a microwell array plate that includes a flat surface solid support, such as a microscope slide and an elastomer gasket that contains an array of through-holes. Distinct surfaces of the elastomer gasket have distinct adhesive properties. The gasket optionally contains a chamfer or another visual marking that allows identification of a more adhesive surface.

The methods and compositions described in this specification may be utilized to analyze various biological samples, including cell-free protein transcription-translation reactions, bacterial cells, mammalian cells, cell culture supernatants, animal models, xenografts, tissue biopsies, biofluids such as serum, plasma and cerebrospinal fluid, and others. The described methods and compositions may be utilized in a broad range of applications including basic research, pharmaceutical drug discovery and drug development, disease diagnostics and prognostics, biomarker discovery and validation, personalized medicine, precision medicine, systems biology and others.

DESCRIPTION OF FIGURES

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A schematically depicts an affinity binding reaction, in which a sample contains a first (target) peptide and a second (reference) peptide and a binding capacity of a bead array is greater that an amount of the first peptide and lower than an amount of the second peptide in the sample.

FIG. 1B schematically depicts an affinity binding reaction, in which a sample contains two distinct peptides and a bead array contains distinct reactive sites that recognize these peptides.

FIG. 1C schematically depicts an affinity binding reaction, in which samples that contain different amounts of a particular peptide are incubated with two bead arrays.

FIG. 1D schematically depicts an affinity binding reaction, in which a sample is consecutively incubated with two bead arrays.

DETAILED DESCRIPTION

The term "bead array" refers to a group that includes at least two reactive sites. A bead array may be located in a container, such as a microcentrifuge tube, or in a well of a multiwell plate, in which case it may be referred to as a suspension bead array. Alternatively, a bead array may be positioned on a solid support, in which case it may be referred to as a planar bead array. A variation of a planar bead array is a bead array, in which individual reactive sites are positioned within size-matching microwells of a microwell array slide, with a single microwell usually being dimensioned to hold no more than one reactive site.

The term "reactive site" refers to a combination of a bead and at least one capture agent that is associated with the bead.

The term "capture agent" refers to a molecule or a molecular complex that is capable of binding a compound. A singular form of the term "capture agent" may refer to a plurality of identical molecules or a plurality of identical molecular complexes. For example, it may refer to a plurality of identical antibody molecules.

The terms "target analyte" and "target" are used interchangeably throughout the instant specification and generally refer to a binding partner of a capture agent. Singular forms of the terms "target analyte" and "target" may refer to a plurality of molecules, e.g. a plurality of peptide molecules.

The terms "peptide" and "polypeptide" are used interchangeably throughout the specification and refer to a combination of at least two amino acids that are linked by an amide bond, which is also known as a peptide bond.

The term "protein" refers to a molecule or a molecular complex that contains at least one polypeptide.

The terms "well" and "microwell" are used interchangeably throughout the instant specification and refer to a topological feature such as a pit or a depression that is able to hold a liquid medium, a particle or both.

The term "microarray" refers to a plurality of spatially separated spots that are positioned on a substantially flat surface of a solid support. Individual spots within a microarray may contain a matrix for mass spectrometry.

In an embodiment, the instant specification describes a method for substantially depleting one or multiple peptide analytes from a sample using affinity capture of the analytes on individual reactive sites of a bead array, optionally followed by MS detection of the captured analytes from individual reactive sites. The described method is useful for quantifying one or more analytes in two or more samples.

Figure 1A:
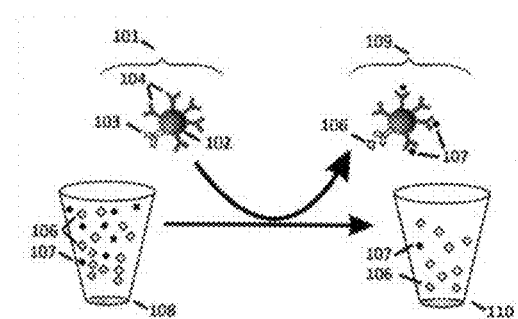
FIGS. 1A through 1D schematically depict various affinity binding reactions that include incubating a sample with a bead array.

In reference to FIG. 1A, a sample 108 contains a first (target) peptide 107 and a second (reference) peptide 106 that is structurally distinct from the first peptide. The sample is brought in contact with a bead array, which contains a reactive site 101. The reactive site contains a bead 102, a capture agent 103 that specifically recognizes the first peptide, and a distinct capture agent 103 that specifically recognizes the second peptide. Contacting the sample with the bead array causes the first peptide and the second peptide to bind to the reactive site and therefore to the bead array. The binding capacity of the bead array and the duration of the contacting step are selected to cause the first peptide to become substantially depleted from the sample, e.g. less than 50%, less than 40%, less than 30%, less than 20%, less than 10%, or less than 5% of the first peptide 107 remains in the sample 110 after the contacting step whereas at least some amount e.g. more than 50% of the second peptide 106 remains in the sample 110. In other words, the binding capacity of the bead array is selected to be: (i) approximately equal to or greater than an amount of the first peptide that is present in the sample and (ii) approximately equal to or lower than an amount of the second peptide that is present in the sample. After the contacting step, the reacted reactive site 109 contains the bound first and second peptides, which are then released individually from the reactive site and measured using MS. The MS data is used to obtain a ratio of the first peptide to the second peptide in the reactive site. The ratio is then used to determine the amount of the first peptide in the sample. In an embodiment, the amount of the first peptide in the sample is determined quantitatively, e.g. 1.2±0.3 pmol. In an embodiment, the amount of the first peptide in the sample is determined as being either above or below a specific pre-determined value, such as being greater than 1.2±0.3 pmol, or being lower than 100±25 fmol.

The method described above enables quantitative measurement of an amount of the target peptide that is present in the sample because a substantial amount, e.g. more than 50%, more than 60%, more than 70%, more than 80%, more than 90%, or more than 95% of the target peptide from the sample is captured by the bead array and a signal from the target peptide is detected by MS along with a signal from the reference peptide, the latter providing a reference, so that the intensity of signal from the target peptide can be readily compared to the intensity of signal from the reference peptide. The quantitative measure of an amount of the target peptide that is originally present in the sample is the intensity of MS signal from the target peptide that is normalized against the intensity of MS signal from the reference peptide. When two or more samples are measured using the above-described method, a difference in the ratio of the target peptide signal to the reference peptide signal observed between the samples is indicative of a difference in the amounts of the target peptide that is present in the corresponding samples.

The sample 108 may be prepared using one of the known methods of bottom-up proteomics, in which a biological material, such as cultured mammalian cells, bacterial cells, tissue biopsy or other is subjected to cell lysis, protein denaturation, disulfide bond reduction, cysteine alkylation and protein digestion, optionally followed by desalting and lyophilization of the produced proteolytic peptides. Sample preparation protocols for bottom-up proteomics are well-known and may be found in numerous publications. A detailed protocol is also provided in this specification. Alternatively, the sample may be prepared using known methods of middle-down proteomics or top-down proteomics.

The target (first) peptide may be produced by enzymatic digestion of a precursor protein that is originally present in the biological material. The target peptide may be selected to monitor abundance of the precursor protein; alternatively, it may be selected to monitor a site-specific post-translational modification (PTM) of the protein, such as phosphorylation, acetylation, methylation, glycosylation, ubiquitination, sumoylation, or other. The target peptide may be also selected to simultaneously monitor several PTMs that are located sufficiently close to each other in the sequence of the precursor protein.

Alternatively, the target peptide may be obtained without performing cell lysis or protein digestion. For example, unfractionated serum and plasma are known to contain large numbers of circulating peptides. Other examples include secreted peptides that are released from cultured mammalian or bacterial cells into a cell culture medium.

The reference (second) peptide may be produced either by enzymatic digestion of a protein that is originally present in the biological sample, by chemical synthesis, or by enzymatically digesting a chemically synthesized precursor peptide. The reference peptide is not required to contain stable isotope-labeled amino acids and is not required to have an amino acid sequence that is substantially similar to the sequence of the target peptide. Preferably the molecular weight of the reference peptide differs from the molecular weight of the target peptide by less than 5 kDa. The reference peptide may be introduced into the sample before, during or after the protein digestion step. The purity of the synthetic reference peptide may vary, however in some cases the peptide purity of 90% or higher is preferred because higher purity peptides generate "cleaner" mass spectra that contain fewer peaks thereby facilitating data interpretation.

The reactive site of the bead array contains a bead and at least two distinct capture agents, e.g. antibodies that are bound to the bead. In an embodiment, the bead is made of porous material such as agarose, cellulose or controlled pore glass and has magnetic properties, which facilitate handling of the bead array. The antibodies are preferably covalently bound to the bead, either directly or via an adapter molecule, such as Protein A, Protein G, Protein A+G, biotin-avidin, etc. The target peptide-specific antibody specifically recognizes an epitope that exists in the target peptide and is thus able to specifically bind the target peptide to the reactive site. The reference peptide-specific antibody specifically recognizes an epitope that exists in the reference peptide and is thus able to specifically bind the reference peptide to the reactive site. A molar ratio of the former antibody to the latter antibody in the reactive site is preferably greater than 1:1, for example it may be greater than 3:1, greater than 5:1, greater than 10:1 or greater than 20:1. The reactive site preferably contains between 100 femtomoles and 5 picomoles of the target peptide-specific antibody and between 5 and 500 femtomoles of the reference peptide-specific antibody.

During the contacting step, the target peptide-specific antibody may specifically bind multiple additional peptides from the sample, if such peptides contain the recognized epitope. This effect enables on-bead multiplexing and analysis of several target analytes from a single reactive site. The additional peptides may arise from incomplete proteolytic digestion of the precursor protein, presence of PTMs, presence of protein isoforms or appearance of the epitope in otherwise unrelated proteins. Preferably, the number of such peptides in the sample is limited, e.g. less than 20 distinct sequences, less than 15 distinct sequences or less than 10 distinct sequences. Binding fewer distinct peptide analytes to a reactive site may be accomplished by (i) selecting an antibody, which recognizes an epitope that is present in a limited number of proteins within the proteome, (ii) performing more complete digestion, i.e. minimizing the amount of partially digested protein fragments, (iii) selecting protein fragments that contain fewer PTMs, etc.

The binding capacity of a reactive site of a bead array for a particular analyte is defined is the maximum amount of the analyte that may specifically bind to the reactive site. A reactive site of the bead array described above contains two distinct antibodies and is therefore capable of binding at least two distinct analytes: the target peptide and the reference peptide. Such reactive site may be characterized as having a binding capacity for the target peptide and a distinct binding capacity for the reference peptide. The analyte binding capacity of a single reactive site may be assumed to be approximately equivalent to an amount of the analyte-specific antibody that is present in the reactive site. For example, a reactive site, which contains 1 picomole of the target peptide-specific antibody and 50 femtomoles of the reference peptide-specific antibody, is capable of specifically binding up to approximately 1 picomole of the target peptide and up to approximately 50 femtomoles of the reference peptide. The analyte binding capacity of a reactive site may be experimentally determined by (1) incubating the reactive site with a sample containing the analyte for an amount of time that is sufficient for binding the analyte to the reactive site and (2) measuring an amount of the analyte that binds to the reactive site. The amount of bound analyte may be measured directly from the reactive site or indirectly by measuring the depletion of the analyte from the reacted sample, e.g. using the colorimetric Bradford assay or absorbance at 280 nm.

In general, the concept of a binding capacity of a bead is explained in various molecular biology and biochemistry textbooks and is well understood by a skilled person. Some Life Sciences vendors, including ThermoFisher Scientific and New England Biolabs also provide online resources that may be used to obtain an estimate of an analyte binding capacity for a specific bead. A link to the article titled "Calculate the Number of Immobilized Proteins per Bead of Agarose Affinity Supports" is provided in the instant specification.

The binding capacity of a bead array for a particular analyte is defined is the maximum amount of the analyte that may specifically bind to the bead array. Bead arrays disclosed in this specification contain reactive sites that have approximately equal binding capacity. Therefore, the binding capacity of the bead array for a particular analyte is approximately equal to the binding capacity of a single reactive site, which is capable of binding the analyte, multiplied by the number of replicate reactive sites that are present in the bead array. For example, the binding capacity of the bead array that contains 5 replicate, i.e. identical reactive sites is 5-fold greater than the binding capacity of one of these reactive sites.

If the target peptide-specific antibody is polyclonal, the reactive site is potentially capable of binding multiple targets that contain distinct epitopes. Such targets may be derived from a single protein or from several different proteins. The binding capacity of the reactive site in this case is assumed to be equivalent to the maximum combined amounts of distinct analytes, which all contain the epitope that is recognized by the corresponding antibody.

The methods described in this specification also enable multiplexed quantitative analysis of peptide and/or protein analytes using simultaneous affinity capture of distinct analytes on distinct reactive sites of the bead array. While a single reactive site is depicted in FIG. 1A, it is noted that the bead array may contain a distinct reactive site that contains the reference peptide-specific capture agent 103 and a capture agent that is distinct from the capture agent 103 and recognizes a target that is distinct from the target 107. The number of such distinct reactive sites in the bead array may be greater than 2, greater than 5, greater than 10, greater than 20, greater than 50 or greater than 100. This enables development of assays that have a multiplexing capacity that is greater than 2-plex, greater than 5-plex, greater than 10-plex, greater than 20-plex, greater than 50-plex, or greater than 100-plex.

The bead array may be made to have an analyte binding capacity that exceeds 1 picomole, 5 picomoles, 10 picomoles, 50 picomoles, or 100 picomoles that is sufficient for depleting low, medium and high abundance peptide and/or protein analytes from biological samples containing up to 50 milligrams (mg) or more of total input protein. The analyte binding capacity of a single reactive site in such bead array may exceed 100 femtomoles, 500 femtomoles or 1 picomole.

The duration of the contacting step, i.e. the duration of incubation of the bead array with the sample is determined, in part, by the diffusion rate of the analyte within the bead of the reactive site. For beads that are sufficiently large, e.g. have diameter that exceeds 200 microns (μm), the duration of the contacting step is preferably more than 1 hour. In some cases, the contacting step may last more than 3 hours, more than 6 hours or overnight (more than 12 hours). The duration of the contacting step may be determined by performing a time course study, as described in detail elsewhere in this specification.

When two or more samples are analyzed using the described methods, accurate results will be obtained if it is ensured that the samples contain approximately equivalent amounts of total input protein. Note that the above methods do not rely on stable isotope labeling for quantitative analysis of protein abundance changes between the samples.

In an embodiment, the instant specification describes a method for depleting a peptide analyte from a sample using affinity capture of the analyte on distinct reactive sites of a bead array, optionally followed by MS detection of the captured analyte from individual reactive sites. The described method is useful for measuring multiple distinct sites within a single protein using the methods of bottom-up proteomics.

Figure 1B:
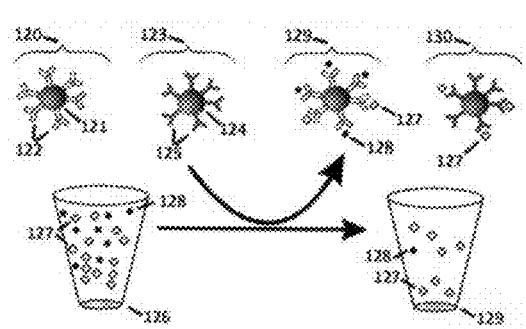

In reference to FIG. 1B, a sample 126 contains a first peptide 127 and a second peptide 128 that is distinct from the first peptide. The sample is brought in contact with a bead array, which contains a first reactive site 120 and a second reactive site 123. The first reactive site contains a bead 121 and a capture agent 122 that specifically recognizes the first peptide and the second peptide. The second reactive site contains a bead 124 and a distinct capture agent 125 that specifically recognizes the first peptide and not the second peptide. The binding capacity of the bead array may be greater than, equal to, or lower than an amount of the first peptide in the sample. The binding capacity of the bead array may be greater than, equal to, or lower than an amount of the second peptide in the sample. Contacting the sample with the bead array causes the first peptide to bind to the first and the second reactive sites and the second peptide to bind to the first reactive site and not the second reactive site. The binding capacity of the bead array may be greater than, equal to, or lower than the amount of the first peptide 127 in the sample 126. Depending upon the binding capacity of the bead array and the duration of the contacting step, the resulting sample 129 may contain an amount of the first peptide, an amount of the second peptide, or both. After the contacting step, the reacted reactive sites 129 and 130 are individually analyzed by MS. Analyzing the first reactive site 129 is used to obtain a ratio of the first peptide to the second peptide in the reactive site. The ratio is then used to determine the amount of the first peptide in the sample. In an embodiment, the amount of the first peptide in the sample is determined quantitatively, e.g. 1.2±0.3 pmol. In an embodiment, the amount of the first peptide in the sample is determined as being either above or below a specific predetermined value, such as being greater than 1.2±0.3 pmol, or being lower than 100±25 fmol.

In an embodiment, the instant specification describes a method for contacting two or more samples, each of which contains at least two distinct peptide analytes, with a corresponding number of bead arrays, each of which contains a reactive site recognizing the peptide analytes, optionally followed by MS detection of the captured analytes from individual reactive sites. The described method is useful for performing epitope mapping assays.

Figure 1C:
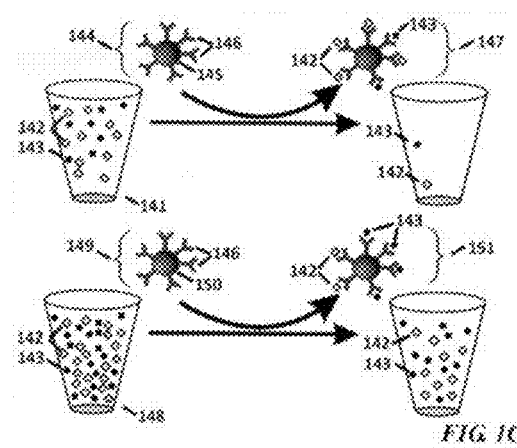

In reference to FIG. 1C, a first sample 141 contains a first peptide 142 and a second peptide 143 that is distinct from the first peptide. A second sample 148 also contains the first peptide and the second peptide. The first sample is brought in contact with a first bead array, which contains a reactive site 144. The reactive site contains a bead 145 and a capture agent 146 that specifically recognizes the first and the second peptides. A binding capacity of the first bead array is greater than the amount of the first and the second peptides in the first sample. The second sample is brought in contact with a second bead array, which contains a reactive site 149. The reactive site contains a bead 150 and the capture agent 146. A binding capacity of the second bead array is lower than the amount of the first and the second peptides in the second sample. The two contacting steps occur concurrently, consecutively or partially overlap in time. After the contacting steps, the reacted reactive site 147 of the first bead array and the reacted reactive site 151 of the second bead array are individually analyzed by MS to obtain a ratio of the first peptide to the second peptide in the corresponding reactive site.

In an embodiment, the instant specification describes a method for consecutively contacting a sample that contains at least two distinct peptide analytes with two or more bead arrays, each of the bead arrays containing a reactive site that specifically recognizes the peptide analytes, optionally followed by MS detection of the captured analytes from an individual reactive site of at least one of the bead arrays. The described method is useful for verifying a quality of the sample, particularly when the analytes in the sample had been subjected to at least one freeze-thaw cycle.

Figure 1D:
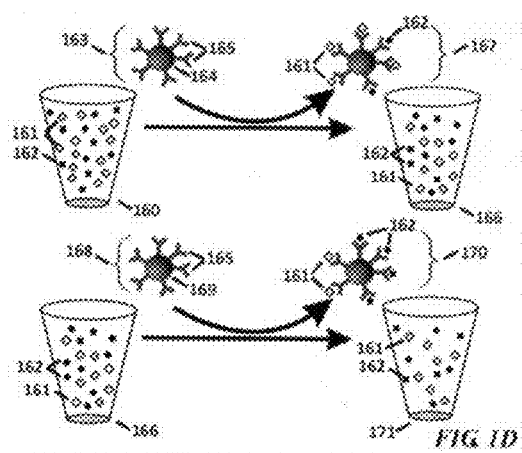

In reference to FIG. 1D, a sample 160 contains a first peptide 161 and a second peptide 162 that is distinct from the first peptide. The sample is brought in contact with a first bead array that contains a reactive site 163. The reactive site contains a bead 164 and a capture agent 165 that specifically recognizes the first and the second peptides. A binding capacity of the first bead array is greater than, equal to, or lower than the amount of the first and the second peptides in the sample. After the contacting step, the reacted sample 166 now contains reduced amounts of the first and second peptides or be depleted of one or both peptides. The sample 166 is subsequently brought in contact with a second bead array that contains a reactive site 168. The reactive site contains a bead 169 and the capture agent 165. The two contacting steps may be separated in time by less than 1 hour, by between 1 hour and 24 hours, by between 1 day and 7 days, by between 1 week and 1 month, by between 1 month and 12 months, or by more than 1 year. The sample 166 may be subjected to 1, 2, 3, 4, 5, or more than 5 freeze-thaw cycles between the two contacting steps. The sample may be stored at room temperature, at about 4° C., at about −20° C., at about −80° C. or below −80° C. between the two contacting steps. The reacted reactive site 167 of the first bead array and/or the reacted reactive site 170 of the second bead array are optionally analyzed by mass spectrometry to obtain a ratio of the first peptide to the second peptide in the corresponding reactive site. In an embodiment, the peptides that are depicted in FIG. 1A, FIG. 1B, FIG. 1C or FIG. 1D and described in the corresponding sections of the specification are unmodified peptides that do not contain a chemical tag. Specifically, they do not contain a chemical group, which is a constituent of one of the labeling reagents known as isotope-coded affinity tag (ICAT®), mass differential tags for relative and absolute quantification (mTRAQ®), isobaric tags for relative and absolute quantitation (iTRAQ®) and TMT™.

After performing the contacting step that is depicted in any of FIGS. 1A through 1D, the reacted bead array(s) is prepared for MS analysis. This includes removing non-specifically bound compounds by washing the reactive sites with a liquid medium that contains a mild detergent, a biological buffer or just deionized water. The washed bead array is then placed on a specially designed plate, which contains an array of microwells that are dimensioned to accept no more than one reactive site per microwell. Placing the bead array on the microwell array plate causes individual reactive sites to sink into individual microwells, thereby creating a planar bead array. Analytes captured on individual reactive sites are released into the respective microwells and mixed with a matrix for MS. For increased efficiency of the MS measurement, the microwell array plate may be converted into a flat surface slide that contains a surface array of spots containing analytes eluted from individual reactive sites. The array of spots is measured by MALDI MS or another type of MS. Some of the array processing steps described in this paragraph are explained in greater detail below.

The microwell array plate is made of a silicone gasket containing an array of through holes that is reversibly attached to a flat surface of a microscope slide. The slide surface is electrically conductive, for example it may contain a surface layer of Indium Tin Oxide (ITO), gold or another conductive material. The watertight seal formed by the silicone gasket in contact with the slide surface prevents liquid diffusion and/or leakage from individual wells, both for aqueous and organic liquids, such as acetonitrile.

The microwell array plate may be subdivided into several regions, e.g. 2, 4, 8, 16, 24, 64 regions using a multi-chamber frame. The individual regions of the microwell array plate may contain beads with analytes derived from distinct biological samples. The multi-chamber frame is removably attached to the microwell array plate using plastic or stainless steel clips.

In an embodiment, the specification describes a reusable microarray substrate for eluting analytes from bead arrays. The reusable microarray substrate includes an elastomer member, i.e. an elastomer gasket that is removably bonded to a flat surface of a solid support, e.g. a microscope slide. The elastomer gasket contains an array of through holes and a visual marking for identifying a surface of the elastomer gasket that is configured for bonding to the solid support. In an embodiment, a diameter of a through hole and a distance between adjacent through holes are less than 600 microns.

The suitable slide is an ITO or gold-coated 25×75×1.1 mm microscope slide that is available from multiple vendors. An exemplary elastomer (silicone) gasket containing an array of through holes and methods of attaching the gasket to the slide to make the microarray substrate are described in the U.S. patent application Ser. No. 16/125,164, publication No. US 2019-0072546 A1. However, the above reference does not teach that the individual components of the microarray substrate may be reusable, that is, may be used multiple times for eluting analytes from bead arrays. Reusing the slide is relatively straightforward and requires a sufficiently thorough wash to remove traces of previously eluted analytes and the matrix from the slide surface. This may be achieved by using a detergent followed by rinsing the slide several times with deionized water. On the other hand, the chemical properties of the elastomer gasket may change significantly between a first use and subsequent uses due to exposure of the elastomer surface to the harsh reagents in the matrix solution, such as strong acid and organic solvent. Importantly, as these reagents may irreversibly change the adhesive properties of the elastomer, they will prevent effective bonding between the slide and the gasket. To overcome this problem, a surface of the elastomer gasket that has been previously exposed to the MALDI matrix solution (the "top" surface) needs to be distinguished from an opposite surface that was in contact with the slide (the "bottom" surface) and therefore has not been exposed to the reagents of the matrix solution, as these surfaces may have distinct adhesive properties. This is achieved by including a visual marking in the gasket that enables unambiguous identification of the surface that is suitable for bonding to the solid support. The visual marking may be provided in the form of a chamfer so that the gasket is asymmetrically shaped.

In an embodiment, an elastomer (e.g. silicone) gasket is originally made such that its "top" surface has different adhesive properties than its "bottom" surface. The top surface is the surface that is facing up when the gasket is attached to a solid support (the microscope slide) and is also the surface that temporarily contacts the multi-chamber frame that is used to sub-divide the microwell array. The bottom surface is the surface that is facing down, contacts the solid support (the microscope slide) and forms a fluidic seal that fluidically separates individual microwells (through holes that are fluidically sealed at the bottom by the solid support). While both the top and the bottom surfaces may be made of a same material, their adhesive properties may be designed to be significantly different. Specifically, the bottom surface may have better self-adhesive properties compared to the top surface, such that the bottom surface readily forms a fluidic seal between microwells (through holes) when attached to a flat surface solid support, while the top surface does not readily form a fluidic seal.

The top surface of a silicone gasket may be made less adhesive than the opposite bottom surface by intentionally increasing its surface roughness. A greater roughness may be achieved by allowing burrs to form around openings into through-holes on the top surface of the gasket, while preventing burrs from forming on the bottom surface. A burr is commonly defined as a raised edge of material that remains attached to a workpiece after a modification process. Methods of both creating and preventing burrs while laser cutting of through holes in silicone elastomer sheets, which are less than 1 mm thick, are well known in the industry. A manufacturer of silicone gaskets such as Grace Bio-Labs (Bend, Oreg.) may be requested to render one surface of the gasket less adhesive than the opposite surface by intentionally allowing burrs to form on the former. Since burrs are only formed around openings into through holes (microwells), an area of the top surface that is located between peripheral through holes and the edges of the gasket remains free of burrs and is therefore capable of forming a fluidic seal when attached to a multi-chamber frame. An aqueous medium placed inside a multi-chamber frame attached to a microwell array plate containing burrs will freely travel between adjacent chambers while micron-sized beads will remain localized within their respective chambers due to size constrains. It is estimated that dimensions of burrs produced by laser cutting in silicone sheets do not exceed 5 microns and often do not exceed 1 micron.

Therefore, the specification describes a microwell array plate that includes a flat surface solid support (e.g. a microscope slide) and a removably bonded elastomer member (e.g. a silicone gasket), in which the elastomer member has a first (bottom) surface and an opposite second (top) surface. The bottom surface is essentially free of burrs and capable of forming a fluidic seal with the solid support. The top surface includes an area that contains burrs around openings into microwells and also includes an area that is essentially free of burrs, the latter area being located between peripheral microwells and the edges of the gasket. The burr-free area is preferably less than 50% of a total area of the top surface and capable of forming a reversible fluidic seal with a multi-chamber frame. The elastomer member further includes a chamfer or a similarly functioning visual marking that enables the burr-free surface to be distinguished from the burr-containing surface.

While regular grade polydimethylsiloxane (PDMS, silicone) is well suited for elastomer gaskets, certain improvements in the gasket performance may be achieved by using fluorocarbon based synthetic rubbers, such as fluoroelastomer FKM, e.g. VITON®, perfluoroelastomer FFKM, or FEPM (tetrafluoroethylene propylene), e.g. AFLAS®. Fluoro-rubbers such as FKM, FFKM and FEPM have good adhesive properties, yet possess greater mechanical sturdiness, which may be beneficial for maintaining regular grid of the microarray spots.

In an embodiment, the instant specification describes a microarray substrate that is coated with a layer of crystalline MALDI matrix. One benefit of using the substrate that is pre-coated with the matrix is that the bead-eluted analytes may better incorporate into the matrix layer that is already positioned on the bottom of individual microwells thereby generating stronger signal from the eluted analytes. Unlike the existing substrates containing pre-spotted matrix, the matrix-coated microarray substrate should have a near neutral pH and not contain a strong acid because low pH may cause premature dissociation of analytes from beads before the beads are positioned into individual microwells. In an embodiment, a near neutral pH is defined as being greater than $5.0\pm0.5$ and lower than $9.0\pm0.5$ pH units. In an embodiment, a near neutral pH is defined as being greater than $6.0\pm0.5$ and lower than $8.0\pm0.5$ pH units.

Another benefit of using the microarray substrate that contains a pre-spotted layer of MALDI matrix is that such microarray substrate is able to more efficiently retain an aqueous medium, e.g. deionized water inside individual microwells and therefore extend an amount of time, during which beads that are placed inside individual microwells remain hydrated. While microwell structures, which are made of silicone, glass, ITO or metals, do not efficiently absorb and retain water, microwell structures, which are made of these materials and additionally contain a surface layer of MALDI matrix, such as α-cyano-4-hydroxycinnamic acid (CHCA) and sinapinic acid (SA), are able to absorb and retain water and/or aqueous solutions for an extended amount of time, e.g. greater than 5 minutes, greater than 10 minutes or greater than 15 minutes under conditions of ambient humidity. The surface layer of MALDI matrix covers both bottom surfaces and sidewalls of individual microwells, as well as the area between openings into individual microwells. In an embodiment, the ambient humidity is higher than 15% relative humidity at a temperature 15° C. or higher.

In an embodiment, the specification describes a method for eluting one or more analytes from a bead array. The described method includes the steps of receiving a bead array, which contains an analyte-bound bead located inside a microwell filled with liquid aqueous medium, and repeatedly or continuously depositing liquid elution medium into the microwell, the elution medium containing a dissolved matrix for mass spectrometry and a solvent, such that a rate, at which the elution medium is being deposited into the microwell, is approximately equivalent to a rate, at which the solvent is escaping from the microwell via evaporation. The bead remains continuously exposed to the solvent and a solution that forms in the microwell has a higher concentration of the dissolved matrix relative to the original elution medium.

While earlier references describe applying MALDI matrix solutions to bead arrays, they generally teach using saturated solutions of matrix, such as 10 mg/ml of CHCA and drying bead arrays between consecutive cycles of matrix application. These methods may not achieve optimal elution of bead-bound analytes in cases where beads are composed of porous materials such as agarose or cellulose.

An improved method of analyte elution, which is described here, involves using a more dilute MALDI matrix solution, e.g. 5 mg/ml of CHCA, applying the matrix solution to a microwell that contains a sufficient amount of aqueous medium, for example deionized water, and matching a rate of depositing the matrix solution into the microwell to a rate of evaporation of a solvent of the matrix solution from the microwell so that the composition of the medium inside the microwell gradually changes from neutral, aqueous medium to acidic, organic-solvent containing medium, which causes the affinity-bound analytes to dissociate from their respective beads and remain in a solution for a specific amount to achieve efficient incorporation of the analytes into the MALDI matrix. The described conditions also prevent splattering and spilling of liquids from the microwells thereby minimizing of eliminating potential cross-talk between neighboring microwells.

Exemplary bead arrays and methods of making bead arrays are described in the U.S. patent application Ser. No. 16/125,164, publication No. US 2019-0072546 A1. The above reference enables making of a bead array that contains affinity beads with bound peptide analytes located inside individual microwells of a microwell array that consists of a removable silicone gasket attached to an ITO-coated glass microscope slide. Individual microwells are filled with deionized water.

The matrix solution for eluting analytes from a bead array should be sufficiently dilute. For the common CHCA matrix, the concentration should be less than 10 mg/ml; specifically, 6 mg/ml or less, 4 mg/ml or less, 2 mg/ml or less, or 1 mg/ml or less. The matrix solution should also contain a sufficiently high concentration of acid; specifically, more than 0.2%, more than 0.3% or more than 0.4% (v/v) of either trifluoroacetic acid (TFA), formic acid (FA) or other suitable acid such as hydrochloric acid. The matrix solution should also contain a sufficiently high concentration of an organic solvent, e.g. at least 30%, at least 40% or at least 50% (v/v) of either acetonitrile, ethanol, isopropanol or methanol. Because the initial concentration of the matrix in the elution medium is sufficiently low, the dilution of the organic solvent, which occurs when the matrix solution-containing aerosol droplets enter water-filled microwells, does not cause immediate crystallization and precipitation of the CHCA matrix yet the pH of the resulting mixed solution that forms in the microwells is sufficiently low, e.g. below 2 due to the high acid content of the matrix solution, which causes rapid acidification and dissociation of the affinity captured peptides from antibody-conjugated beads and subsequent mixing of the eluted peptides with the matrix-containing solution inside the microwells.

The elution medium, i.e. the matrix solution is being continuously deposited into the microwells via repeated cycles of applying an aerosol containing microdroplets of the matrix solution into microwells. That process occurs simultaneously with a process of continuous evaporation of the solvent of the matrix solution from the microwells thereby causing an increase in the concentration of the dissolved matrix in the microwells to the point where the matrix concentration in the mixture of the aqueous medium and the elution medium eventually exceeds the matrix concentration in the original elution medium. Once the matrix deposition process stops, there is provided a sufficient time for the solvent to evaporate, which causes the matrix to precipitate and co-crystallize with the eluted peptide analytes. Because the analyte elution from beads occurs before the matrix crystallization, the eluted peptides are provided a sufficient amount of time to thoroughly mix with the dissolved matrix, e.g. for more than 5 minutes, more than 10 minutes, more than 20 minutes, or more than 30 minutes. If desired, the matrix crystallization process may be visually monitored using optically transparent ITO-coated glass slides.

The deposition of the elution medium into the bead array should be performed using conditions that prevent splattering and spilling of the medium from the microwells in order to maintain the spatial resolution of the array and to prevent cross-talk between adjacent spots within the array. Specifically, the microdroplets containing the elution medium should have sufficiently low velocity to minimize their impact upon contact with the liquid medium inside the microwells, which may be achieved by selecting sufficiently low flow rate of the carrier gas that is used to generate the aerosol. Other conditions may include selecting an optimal distance between the nozzle that generates the microdroplets and the surface of the array. In an embodiment, the distance is greater than 30 mm, greater than 45 mm or greater than 60 mm.

Furthermore, if the aerosol containing the elution medium is generated using a programmable device, e.g. a MALDI matrix sprayer, values of the parameters that are supplied to the device, such as the speed of matrix deposition and the density of matrix solution per area unit should be selected according to an ambient air humidity level. When the values are properly selected, the microwells do not overflow because the addition of elution medium into the microwells is matched by the escape of the solvent of the elution medium from the microwell via evaporation. For the user convenience, the programmable device may include a hygrometer that is operably connected to the device.

The values of parameters provided to the programmable device may be further selected according to the chemical composition of the analyte, the chemical composition of the elution medium and/or the chemical composition of the aqueous medium.

Once the matrix solution application stops, the residual solvent is allowed to completely evaporate, which causes the matrix to precipitate and co-crystallize with the eluted peptide analytes. The beads become dry and may be removed from their respective microwells by compressed air, for example using a regular duster can. The bead removal should take place prior to separating the gasket from the slide, although applying the air to dislodge beads from the slide after the gasket had been detached is also possible.

Figure 2A:
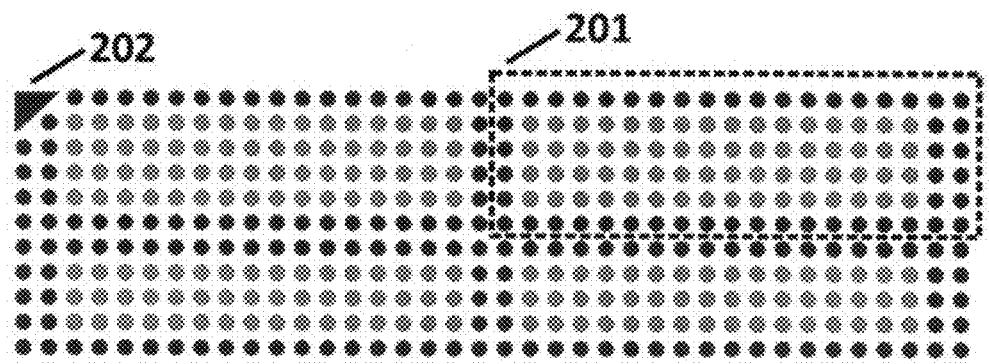
FIG. 2A schematically depicts a microarray of spots that contain MS matrix.

The methods described above enable fabrication of a microarray that contains multiple discrete spots located on a flat surface of a solid support, e.g. a microscope slide. Such microarray is schematically depicted in FIG. 2A. All microarray spots contain MS matrix and at least some spots additionally contain one or multiple analytes transferred from a bead array. A spot that contains or is suspected of containing an analyte is visibly distinct from a spot that is devoid of the analyte. The analyte-containing spot is also distinct from a spot that contains or is suspected of containing a mixture of analytes, as explained in greater detail below. The microarray may contain a smaller size section 201 that contains analytes obtained from a single biological sample. The microarray may contain distinct sections that contain analytes obtained from distinct biological samples. The microarray may further contain a fiducial 202, as described in greater detail below.

Figure 2B:
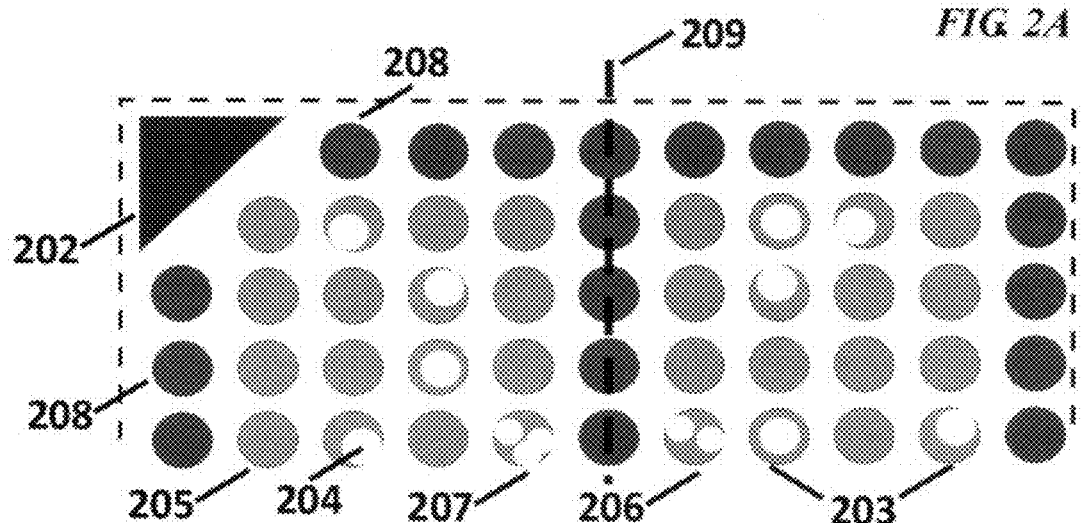
FIG. 2B schematically depicts a section of a microarray, in which spots that contain an analyte or are suspected of containing an analyte are visibly distinct.

In reference to FIG. 2B, when a bead occupies a certain portion of a bottom surface within a microwell, it may prevent the matrix from precipitating and forming crystals directly underneath. After the bead is removed, the pattern of matrix distribution within each spot is revealed. A spot 203 that previously contained a bead exhibits a characteristic donut or crescent shape because it includes an inner region 204 that has a visibly lower density of matrix coverage; in some cases, the inner region 204 may be substantially free of the matrix. An area of such inner region may be greater than 5%, greater than 10%, greater than 20%, greater than 30%, greater than 40%, greater than 50%, greater than 60%, greater than 70%, greater than 80%, or greater than 90% of a total area of the spot, being determined by a combination of several factors: the bead diameter, the microwell diameter, surface properties of the microarray slide, chemical composition of the matrix solution and conditions of the matrix crystallization process. By contract, a spot 205 that did not initially contain a bead exhibits a substantially uniform pattern of the matrix coverage compared to the former spot. The distinct shapes of the two types of spots are visually distinguishable and may be used to selectively measure spots that contain or are suspected of containing an analyte of interest while excluding spots that are not expected not contain such analyte.

Furthermore, an analyte-containing spot 203 is also visibly distinct from spots 206 and 207 that contain or are suspected of containing a mixture of analytes. The mixing of analytes may occur if two, three or more beads occupy a single microwell. In such case, a pattern of matrix distribution within a spot reveals two or three distinct inner regions that have a visibly lower density of matrix coverage or are free of the matrix. The distinct shape of a spot that previously contained multiple beads and therefore contains or is suspected of containing a mixture of analytes may be used to exclude such spot from analysis by MS. Alternatively, it may be used in data analysis to indicate that multiple analytes were co-eluted from several beads in a particular spot.

Due to inherent heterogeneity of the matrix-analyte crystallization process, the spatial distribution of an analyte within an analyte-containing spot may not be known prior to MS analysis, particularly if the analyte is not fluorescent. However, it is noted that spots, which are prepared using the above-described method and contain an analyte, consist of an upper layer and a lower layer, both layers containing the matrix yet the upper layer containing a greater amount of the analyte compared to the lower layer. The higher analyte concentration in the upper layer of a spot may be experimentally verified by continuously acquiring MS data from the spot and detecting a decrease in intensity of the analyte signal after a top layer of the spot has been consumed, in some cases without visibly depleting the matrix in the spot. Thus, it is possible to limit the data acquisition to the upper layer of a particular spot to reduce the amount of time needed to interrogate the spot.

In addition to the analyte-devoid spots that are randomly positioned throughout the microarray, the microarray may contain at least one row and/or column that consists of spots 208 that are devoid of bead-eluted analytes and have a visibly distinct pattern of the matrix coverage. Such row and/or column(s) is located on a periphery of the microarray or at a boundary 209 that separates sections of the microarray that contain analytes obtained from distinct samples. Its location coincides with a location of a divider of a multi-well chamber. As the multi-well chamber is pressed against the elastomer gasket during the sample preparation process, through-holes of the gasket that are located directly under the divider do not receive water or beads. Accordingly, when the bead array assembled on a microwell array plate is subsequently contacted with the matrix-containing aerosol, at least one row and/or column contains wells that are initially dry and do not contain beads. The pattern of matrix coverage in such wells is noticeably different from the wells that contained water, even if both types of wells do not contain a bead. The location of an empty row and/or column is determined by the layout of the multi-well chamber and may be further verified by visual detection. During MS data acquisition process, spots within such row and/or column may be excluded from the measurement to provide significant time savings. In the context of current specification, a row or a column of a microarray is defined as a group that consist of at least 3 microarray spots that are aligned horizontally or vertically, respectively.

Furthermore, the molecular structure of matrix crystals formed in locations that were initially dry is different from the molecular structure of matrix crystals in locations that initially contained the aqueous medium resulting in noticeable differences in the corresponding mass spectra. Specifically, a mass spectrum recorded from a spot 208 that is produced by placing the MS matrix solution into a dry microwell exhibits multiple strong peaks in the spectral region below 1400 m/z, which are assigned to various matrix clusters containing sodium and potassium ions. By contrast, a mass spectrum recorded from a spot 205 that is produced by placing the matrix solution into a water-filled microwell exhibits much weaker matrix clusters peaks that are often not detectable above 800 m/z. Therefore, in applications where multiple spots of a microarray are analyzed by MS, the location of a row and/or column that separates sections of the microarray containing analytes from different biological samples may be determined by detecting intense matrix cluster signals from individual spots within such row and/or column. The described procedure may be used for microarray gridding.

The asymmetrical shape of the elastomer gasket containing a chamfer allows placing a fiducial marker into the microarray during the process of matrix application. The fiducial 202 contains the matrix and has a shape that is visibly distinct from a shape of a microarray spot. A position of the fiducial coincides with a location of the chamfer. The fiducial is produced at the same time as the analytes are being eluted from the bead array during the matrix application process. Thus, the quality of matrix crystals in the fiducial should be essentially identical to the quality of matrix crystals in the individual microarray spots and may be used to monitor the conditions of the matrix application. Once created, the fiducial may be used to properly orient the microarray before placing the microarray slide into an MS instrument. Alternatively, the fiducial may be measured during MS imaging of the microarray and its position used to properly orient the microarray image for subsequent data analysis.

Individual spots of the described microarrays may be 1000 microns or less, 600 microns or less, 400 microns or less, or 200 microns or less.

Distinct patterns of analyte-containing spots (203) and analyte-devoid spots (205) within each microarray are due to the random nature of a process of beads being placed inside microwells, the number of available microwells being greater than the number of beads. Such distinct patterns of analyte-containing spots and/or analyte-devoid spots may be used for positional encoding of individual microarrays. Specifically, X-Y coordinates of either all or some of analyte-containing spots and/or all or some of analyte-devoid spots in a microarray may be associated with various information about the microarray, including for example identities of analytes present in the microarray, a date of making the microarray, etc. Alternatively, an optical image of the microarray rather than X-Y coordinates may be associated with the information about the microarray. The concept of positional encoding of a microarray by using the unique patterns of analyte-containing and analyte-devoid spots is also described in Experimental Examples.

In summary, the instant specification describes several improvements related to making, using and analyzing bead arrays by MS.

In an embodiment, the specification describes a microarray substrate comprising an elastomer member that is removably bonded to a substantially flat surface of a solid support, the elastomer member containing a plurality of through holes and a visual marking, wherein a diameter of a through hole and a distance between adjacent through holes are less than 600 microns and the visual marking is suitable for identifying a surface of the elastomer member that is configured for bonding to the solid support. In an embodiment, the elastomer member is asymmetrically shaped. In an embodiment, the elastomer is a fluoro-elastomer. In an embodiment, the surface configured for bonding to the solid support and an opposite surface of the elastomer member have distinct adhesive properties. In an embodiment, portions of the elastomer member and the solid support are coated with a surface layer that contains a crystalline matrix for MS and does not contain a strong acid.

In an embodiment, the specification describes a method for making a reusable microarray substrate, the method comprising the step of bonding an elastomer member to a substantially flat surface of a solid support, the elastomer member containing a plurality of through holes and a visual marking, wherein a diameter of a through hole and a distance between adjacent through holes are less than 600 microns, and the visual marking is used to orient the elastomer member relative to the solid support prior to the bonding step. In an embodiment, the visual marking is suitable for identification of a surface of the elastomer member that was not previously exposed to a solution containing a matrix for MS. In an embodiment, the method further comprises the step of contacting the elastomer member and the solid support with an aerosol, the aerosol containing a dissolved matrix for MS and not containing a strong acid, the contacting step being performed after the bonding step.

In an embodiment, the specification describes a microarray comprising a plurality of discrete spots positioned on a substantially flat surface of a solid support wherein a spot that contains or is suspected of containing an analyte is visibly distinct from a spot that is devoid of the analyte and all spots contain a matrix for MS. In an embodiment, the analyte-containing spot includes an inner region that has a visibly lower density of the matrix coverage. In an embodiment, an area of the inner region is greater than 20% of a total area of the analyte-containing spot. In an embodiment, the analyte-containing spot is further visibly distinct from a spot that contains or is suspected of containing a mixture of analytes. In an embodiment, the analyte-containing spot comprises an upper layer and a lower layer, both layers containing the matrix, the upper layer containing a greater amount of the analyte compared to the lower layer. In an embodiment, the microarray contains at least one row and/or column that consists of spots that have a visibly distinct pattern of the matrix coverage, the at least one row and/or column being located on a periphery of the microarray or at a boundary that separates sections of the microarray that contain analytes obtained from distinct samples. In an embodiment, the microarray further comprises a fiducial, the fiducial containing the matrix and having a shape that is visibly distinct from a shape of a microarray spot. In an embodiment, dimensions of individual microarray spots are 400 microns or less.

In an embodiment, the specification describes an analytical method, the method comprising the steps of receiving a microarray, the microarray comprising a plurality of discrete spots positioned on a substantially flat surface of a solid support, all spots containing a matrix for MS, optically identifying a spot that includes an inner region that has a visibly lower density of the matrix coverage, optically identifying a spot that has a substantially uniform pattern of the matrix coverage, analyzing the former spot by MS, and excluding the latter spot from analysis by MS. In an embodiment, the excluded spot is located on a periphery of the microarray or at a boundary that separates sections of the microarray that contain analytes obtained from distinct samples. In an embodiment, the method further comprises the step of optically identifying and subsequently excluding multiple spots from the analysis by MS, the multiple spots forming at least one row and/or column within the microarray, the at least one row and/or column being located on a periphery of the microarray or at a boundary that separates sections of the microarray that contain analytes obtained from distinct samples.

In an embodiment, the specification describes a method for eluting an analyte from a bead array, the method comprising the steps of receiving a bead array, the bead array comprising a bead that is positioned in a microwell, the bead being associated with an analyte, the microwell containing an aqueous medium, and repeatedly depositing an elution medium into the microwell, the elution medium comprising a dissolved matrix for MS and a solvent, wherein a rate, at which the elution medium is being deposited into the microwell, is approximately equivalent to a rate, at which the solvent is escaping from the microwell via evaporation, such that: the bead is continuously exposed to the solvent and a solution that forms in the microwell has a higher concentration of the dissolved matrix relative to the elution medium. In an embodiment, a concentration of the matrix in the elution medium is less than 10 mg/ml. In an embodiment, the solvent contains more than 0.2% of a strong acid. In an embodiment, the bead is continuously exposed to the elution medium for at least 5 minutes. In an embodiment, elution medium is being deposited into the microwell using conditions that substantially prevent splattering and spilling of the elution medium from the microwell. In an embodiment, the elution medium is being deposited using a programmable device that is capable of producing an aerosol, the method further comprising the step of supplying at least one value to the programmable device, the at least one value being selected according to an ambient air humidity level. In an embodiment, the at least one value is further selected according to at least one of a chemical composition of the analyte, a chemical composition of the elution medium, and a chemical composition of the aqueous medium. In an embodiment, the programmable device is operably connected to a hygrometer.

In an embodiment, the specification describes a method for eluting an analyte from a bead array, the method comprising the steps of receiving a bead array, the bead array comprising a bead that is positioned in a microwell, the bead being associated with an analyte via an acid-labile bond, the microwell containing an aqueous medium, depositing a first amount of an elution medium into the microwell, the elution medium comprising a dissolved matrix for MS and a solvent, and allowing the aqueous medium and the elution medium to form a mixture, the mixture being sufficiently acidic to cause the analyte to dissociate from the bead, depositing a second amount of the elution medium into the microwell such that a concentration of the matrix in the mixture exceeds a concentration of the matrix in the elution medium and allowing the solvent to evaporate from the microwell thereby causing the matrix to co-crystallize with the analyte.

In an embodiment, the specification describes a method for eluting an analyte from a bead array, the method comprising the steps of receiving a bead array, the bead array comprising a bead that is positioned in a microwell, the bead being associated with an analyte, the microwell containing an aqueous medium, depositing an elution medium into the microwell, the elution medium comprising a dissolved matrix for MS and a solvent, wherein the aqueous medium and the elution medium are allowed to form a mixture under conditions that substantially prevent the matrix from precipitating from the mixture, and providing a sufficient amount of time to allow the solvent to escape the microwell via evaporation thereby causing the dissolved matrix to precipitate. In an embodiment, the amount of time is greater than 10 minutes.

The present disclosure is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the present disclosure, and are not intended to limit the scope of the present disclosure nor are they intended to represent that the experiments below are all or the only experiments performed. Efforts have been made to ensure accuracy with respect to numbers used (e.g. amounts, temperature, volume, time etc.) but some experimental errors and deviations should be accounted for.

EXAMPLES

Materials and Equipment

N-Hydroxysuccinimide (NHS)-activated magnetic agarose beads, ITO (Indium Tin Oxide) and gold-coated microscope slides, silicone gaskets and multi-well chambers and methods of assembling bead arrays are described in the U.S. patent application Ser. No. 16/125,164, publication No. US 2019-0072546 A1.

Unless noted otherwise, consumables such as microcentrifuge tubes, pipette tips, weigh boats etc., were standard research grade. Reagents such as organic solvents, acids, salts, buffers, detergents, MALDI matrices etc, were standard research grade with a purity of 99% or higher and used as received from the manufacturer without further purification. Standard lab equipment included a microcentrifuge, a microplate centrifuge, magnetic tube racks, microtiter plate shaker, vortexer, etc.

Programmable robotic liquid sprayer iMatrixSpray that is capable of dispensing MALDI matrix solutions was from Tardo GmbH (Subingen, Switzerland).

Experimental Results

Some of the experiments performed using the compositions and methods disclosed in this application and the resulting experimental data are described below.

Example 1

Microarray Reactive Site Containing Two Distinct Capture Agents

Rabbit monoclonal antibody recognizing p44 and p42 MAP Kinase (Erk1 and Erk2) when dually phosphorylated at Thr202 and Tyr204 of Erk1 (Thr185 and Tyr187 of Erk2), and/or singly phosphorylated at Thr202 was purchased from Cell Signaling Technology (Danvers Mass.), catalog number 4370 (D13.14.4E). Rabbit monoclonal antibody recognizing phosphorylated Thr1462 in human Tuberin (TSC2) was also from Cell Signaling Technology, catalog number 3617 (5B12). The #3617 and #4370 antibodies were supplied by the manufacturer in BSA-free, glycerol-free and Tris-free medium. After receiving the antibody stocks, their concentrations were adjusted to 1 mg/ml by diluting with 1× PBS. An antibody mixture was prepared by combining stocks containing the #4370 and #3617 antibodies in 95:5 ratio (w/w). An amount of approximately 7 micrograms of the combined antibody mixture was used for direct conjugation to 100 of Protein A+G activated magnetic agarose beads. Individual beads were in the 375 to 400 micron diameter range. The beads containing the mixture of two antibodies were subsequently cross-linked to the beads using the previously published procedure utilizing dimethyl pimelimidate dihydrochloride (DMP). An amount of capture reagent per single bead was estimated to be between 400-500 fmol and 20-25 fmol for the #4370 and #3617 antibodies, respectively.

The beads were subsequently transferred into 1× PBS supplemented with 0.03% sodium azide and stored at 4° C. until ready to use.

Example 2

Measuring the Analyte Binding Capacity of a Bead Array

Multiple identical reactive sites containing the antibodies #3617 and #4370 were prepared as described in the previous Example. Several identical bead arrays were assembled by combining 5 replicate reactive sites per bead array. The binding capacity of each bead array is assumed to be 5-fold greater than the binding capacity of a single reactive site. It was experimentally determined that the #4370 antibody is capable of specifically binding several peptide targets containing the recognized epitope, including peptides VADPDHDHTGFL[pT]EYVATR (SEQ ID NO: 1) (fragment of Erk2, singly phosphorylated at Thr185), VADPDHDHTGFL[pT]E[pY]VATR (SEQ ID NO: 2) (fragment of Erk2, doubly phosphorylated at Thr185 and Tyr187), IADPEHDHTGFL[pT]EYVATR (SEQ ID NO: 3) (fragment of Erk1, singly phosphorylated at Thr202) and IADPEHDHTGFL[pT]E[pY]VATR (SEQ ID NO: 4) (fragment of Erk1, doubly phosphorylated at Thr202 and Tyr204). The above peptides are derived from their respective precursor proteins via proteolytic digestion using trypsin. In addition, it was experimentally determined that the #4370 antibody is capable of specifically binding various synthetic peptides containing the recognized epitope, including peptides that are both larger and smaller than the tryptic fragments of Erk1 and Erk2.

The antibody #3617 specifically recognizes phosphorylated Thr1462 in full-length human Tuberin. It was experimentally determined that the #3617 antibody is not cross-reactive and does not specifically recognize endogenous peptides that are present in digested mammalian cell lysates, human or mouse tissue lysates or biofluids such as serum and plasma. It was also determined that the #3617 antibody does not specifically recognize the corresponding proteolytic fragment of human Tuberin after digestion with trypsin, likely due to the loss of the epitope. A synthetic peptide GSPSGLRPRGY[pT]ISDSAPSR (SEQ ID NO: 5) where [pT] denotes phosphorylated threonine was synthesized by New England Peptide (Gardner, Mass.) and supplied in greater than 95% purity. The peptide amount was quantified using amino acid analysis (AAA). The synthetic peptide contains the phospho-Tuberin epitope that is recognized by the #3617 antibody. The synthetic peptide is not tryptic as it contains an additional amino acid, the N-terminal Gly that is not found in the precursor human protein and also contains a missed trypsin cleavage site. Accordingly, when the synthetic peptide is spiked into a sample, the sample will contain more than 95% of a single peptide, i.e. the synthetic peptide that is specifically recognized by the #3617 antibody and less than 10%, in fact less than 5% of other peptides that are recognized by the #3617 antibody, the other peptides being impurities of the synthetic peptide. The synthetic peptide is detected by MALDI TOF MS near 2141.0 m/z (singly charged ions) and 1071.0 m/z (doubly charged ions). Minimizing the presence of additional peptides in the sample to below 5% enables acquisition of very clean MS spectra that exhibit a single strong peak at the m/z of singly charged ion and a smaller peak at the m/z of doubly charged ion.

The binding capacity of the assembled bead array was evaluated in several experiments. Measured amounts (1 pmol to 10 pmol) of the synthetic peptide described in the previous paragraph were mixed with a solution containing approximately 50 pmoles of trypsin-digested Bovine Serum Albumin (BSA) and incubated with the bead arrays. The bead arrays were incubated with the peptide-containing solution for at least 1 hour and at most 24 hours. The analyte signal from individual reactive sites beads was measured by MS as described elsewhere in the specification. The amount of residual synthetic peptide in a particular sample after an incubation with a bead array was measured using the #3617 antibody and the conventional dot blot assay. In some experiments, the reacted solution was saved and subsequently incubated with a new bead array.

It was experimentally determined that a bead array containing 5 identical reactive sites, each of the reactive sites containing 5% of the #3617 antibody, has a binding capacity that is less than 15% of 1 pmol of the corresponding synthetic peptide. The estimate is derived from both the MS data, which measures the bound peptide, and the dot blot data, which measures the peptide remaining in the sample after the incubation. The estimate is also in agreement with the calculated amount of the antibody in the bead array. The results indicate that a bead array containing 100 reactive sites has a binding capacity that is less than 50% of 10 pmol of the #3617-specific synthetic peptide. For greater multiplex assays, the amount of synthetic peptide in a sample may be increased to more than 50 pmol or even more than 100 pmol.

The binding capacity of the same bead array for the Erk1/2-derived peptides is significantly higher due to a greater amount of the #4370 antibody compared to the #3617 antibody. It is estimated that the bead array is capable of binding at least 2.5 pmol of a combined amount of peptides that contain the epitope recognized by the former antibody. That includes both singly- and doubly-phosphorylated fragments of Erk1 and Erk2.

Example 3

Preparing a Biological Sample for MS Analysis

The procedures for culturing human MKN45 cells, lysing the cells, digesting the cell lysates and purifying the proteolytic peptides are provided in the U.S. patent application Ser. No. 16/125,164, publication No. US 2019-0072546 A1. The procedure for obtaining proteolytic peptides from a human tissue (adult brain) is provided below.

A total of 100 mg of adult human male brain tissue was received from the Maine Medical Center BioBank (Scarborough, Me.). The tissue sample was cooled in liquid nitrogen for 15 minutes and subsequently pulverized using the Bessman tissue pulverizer. The pulverized material was transferred to a clean polypropylene tube, the urea lysis buffer was added to the sample to bring the total protein concentration to 2 mg/mL. In some cases, further homogenization was performed using a bead beater and 0.1 mm zirconia/silica beads (BioSpec Products, catalog number 11079101z). The complete the tissue lysis, the mixture was sonicated using a microtip at 15 W output with 3 bursts of 15 sec each with cooling on ice for 1 min between each burst. The lysate was cleared by centrifugation at 4,800 g for 15 min at 15° C. and the supernatant containing the protein extract transferred into a new tube. At this stage the tissue lysate was frozen at −80° C. and stored for several weeks. Protein denaturation, reduction, alkylation, desalting and lyophilization procedures for tissue-derived proteins were identical to the previously described procedures for cell culture-derived proteins. The lyophilized peptides can be stored frozen at −80° C. for several months.

Example 4

Obtaining an Estimate of the Total Protein Content of a Sample

A lyophilized sample containing peptides obtained by proteolytic digestion of 2 mg of MKN45 cell lysate was stored at −80° C. The sample was dissolved in 200 µL of the binding buffer containing 1M KCl and 100 mM Tris-HCl pH 8.0 in deionized water. The sample was dissolved by pipetting up and down several times and subsequently centrifuged at 14000 RPM on a tabletop centrifuge for 5 minutes at 4° C. 2 µL of the supernatant was measured on DS-11 FX+ spectrophotometer/fluorometer (DeNovix) using the Absorption 280 application provided with the instrument. Two to three replicate measurements were performed on each sample. The measured sample absorption at 280 nm was subsequently converted into the protein concentration using the formula 1OD A280=1 mg/ml and the total protein (peptide) amount in the sample was calculated by multiplying the protein concentration by the sample volume.

While preparing two or more samples for MS analysis, each sample was measured as described above and the protein (peptide) content of each sample was made to be approximately equal by adjusting the sample volume.

Example 5

Multiplexed Affinity Binding of Peptide Analytes to a Bead Array 1 mg of the digested MKN45 cell lysate dissolved in 200 µL of the binding buffer was mixed with 1 pmol of the synthetic peptide GSPSGLRPRGY[pT]ISDSAPSR (SEQ ID NO: 5) and the mixture transferred into a single well of an EPPENDORF® 96 well plate. The well was subsequently sealed using PARAFILM® tape to prevent solvent evaporation. Magnetic microbeads conjugated to #4370 and #3617 antibodies were added to the lysate. The 96 well plate was inserted into the EPPENDORF® Thermomixer C and the microbeads incubated with the lysate for at least 3 hours and at most 24 hours at 4° C. and shaking at 1200 RPM. Individual reactive sites of the bead array were subsequently measured by MALDI TOF MS. Post-data acquisition calibration of each mass spectrum was performed using m/z values of the singly- and doubly-charged ions of the synthetic peptide. Signals from both the Erk1 and Erk2-derived peptides and from the synthetic peptide were detected in the mass spectra. It was observed that incubation times longer than 3 hours provided more stable ratios of signals from a specific Erk1 or Erk2-derived peptide to the signal from the synthetic peptide, indicating that kinetics of binding of the Erk1 and Erk2-derived peptides and the synthetic peptide to individual reactive sites of the bead array may require more than 3 hours to reach the equilibrium.

Example 6

Reusable Microarray Substrate Containing a Chamfer

A reusable microarray substrate was produced by affixing a silicone rubber gasket, which contained an array of through holes, to a clean flat surface of an ITO-coated glass microscope slide. The gasket was made of a standard grade polydimethylsiloxane (PDMS), the material found in press-to-seal SILICONE ISOLATORS™ products from Grace Bio-Labs (Bend, Oreg.). The custom gaskets were produced by Grace Bio-Labs. Red silicone gaskets had dimensions of 24 mm×74 mm×0.5 mm and contained a square grid array of 26×88 microwells. An internal diameter of each microwell was 0.5 mm with adjacent microwells separated by a distance of 0.3 mm (0.8 mm measured as center-to-center). An area of approximately 1.5 mm between peripheral wells and the edges of the gasket contained no wells. Clear silicone gaskets had dimensions of 24 mm×74 mm×0.25 mm and contained a square grid array of 48×148 microwells throughout the gasket area. An internal diameter of each microwell was 0.25 mm with adjacent microwells separated by a distance of 0.5 mm measured as center-to-center.

Silicone gaskets received from the manufacturer were trimmed to create a visual marking in the form of a chamfer (FIG. 3) to distinguish the "top" surface of the gasket, which may be repeatedly exposed to the MALDI matrix solution, from the "bottom" surface, which contacts the microscope slide and should not be exposed to the matrix solution. The visual marking, e.g. the asymmetrical shape of the silicone gasket was used to properly orient the gasket relative to the microscope slide when assembling a new microarray substrate and also when assembling a microarray substrate using a gasket that has been previously exposed to the MALDI matrix solution. In this Example, the bottom surface of the silicone gasket shown in FIG. 3 is suitable for bonding to a microscope slide when the gasket is horizontally oriented and the chamfer is found in the upper left corner of the gasket.

It was experimentally verified that while adhesive properties of the "top" surface of the silicone gasket had noticeably changed following an exposure to the MALDI matrix solution, no silicone contamination of samples containing bead-eluted analytes was detected, even after repeatedly using the gasket.

Figure 3:
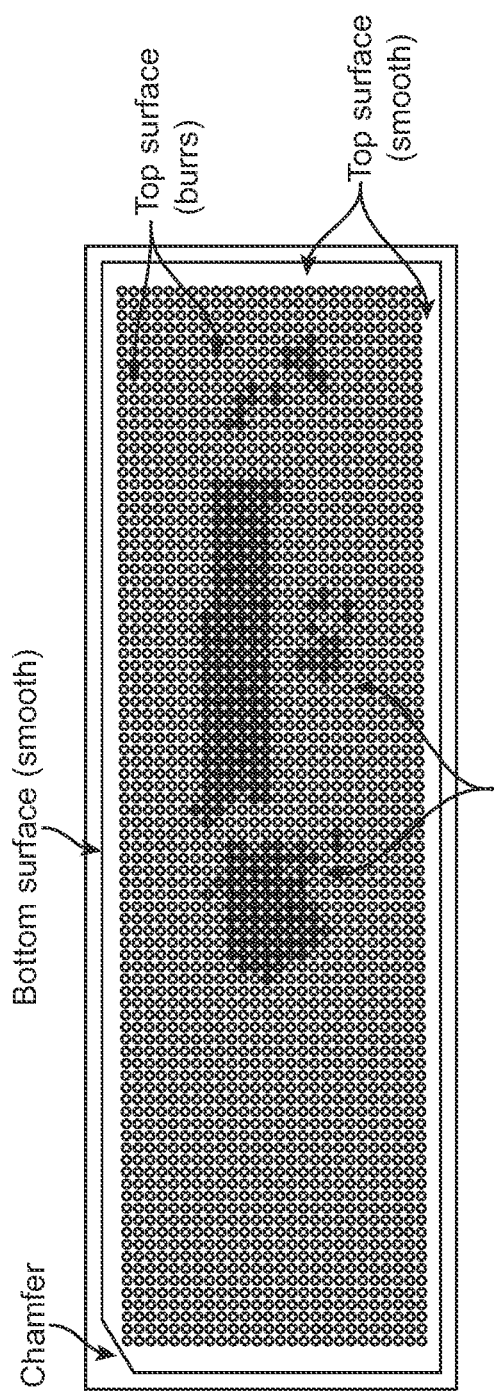
FIG. 3 is a photograph of a reusable microarray substrate.

Further in reference to FIG. 3, it is noted that the "bottom" surface of the gasket is sufficiently smooth throughout its entire area, possesses self-adhesive properties and forms a fluidic seal when bonded to the solid support (the microscope slide). A portion of the "top" surface contains burrs that surround openings into individual microwells (through holes) and is therefore not self-adhesive within an area that contains the openings into microwells. A portion of the "top" surface, which is located between peripheral microwells and edges of the gasket, lacks burrs, is smooth, self-adhesive and capable of forming a fluidic seal. Approximate locations of the corresponding portions of the "top" surface are labeled by arrows in FIG. 3.

Example 7

Microarray Substrate Containing a Layer of MALDI Matrix

A reusable microarray substrate containing a silicone rubber gasket attached to a gold-coated microscope slide was prepared as described in the previous Example. The microarray substrate was subsequently coated with a layer of CHCA MALDI matrix according to the previously described method of matrix deposition using iMatrixSpray. The matrix solution contained 10 mg/ml CHCA in 50% acetonitrile and did not contain a strong acid, such as TFA or FA. The pH of the matrix solution was near 6. 10 cycles of matrix deposition produced a sufficiently dense surface layer of CHCA matrix that fully covered the bottom and sidewalls of individual microwells as well as a surface area of the gasket between openings into microwells. The size of individual CHCA matrix crystals was less than 50 microns. Because of the absence of a strong acid in the matrix solution, hydrating the matrix-coated microarray substrate with deionized water kept the pH of the liquid medium on the surface and inside individual microwells near 6.

A microarray substrate containing a surface layer of MALDI matrix has several useful properties. Specifically, the matrix layer prolongs evaporation of water from the microwells, allows easier removal of droplets of water from the upper surface of the microarray substrate and may improve incorporation of bead-eluted peptide analytes into MALDI matrix, similarly to the sandwich method of MALDI sample preparation.

The protocol for eluting analytes from bead arrays using a pre-coated microarray substrate is similar to the protocol using a regular microarray substrate, although fewer cycles of matrix application may be required with the former. Because the pre-coated matrix layer does not contain a strong acid, the bead-bound analytes are not eluted from a bead array until the acidic pH matrix solution is applied.

This Example describes a method of preparing a bead array for analysis by mass spectrometry that includes the following steps: providing a microarray substrate, which includes an elastomer member (silicone rubber gasket) that is bonded to a flat surface solid support (gold-coated microscope slide), the microarray substrate containing an array of microwells (through holes within the silicone gasket), the bottom surface and the sidewalls of individual microwells coated with a surface layer of MALDI matrix (CHCA, SA or other), which does not contain a strong acid; assembling a bead array by placing beads in an aqueous solution (e.g. deionized water) into individual microwells of the microarray substrate such that pH of the aqueous solution inside individual microwells remains near neutral; and once the bead array is assembled, contacting the bead array containing the aqueous solution with an aerosol containing acidic MALDI matrix solution, wherein the aerosol contacting step is initiated more than 3 minutes, more than 5 minutes or more than 10 minutes after the bead array is assembled. Despite the time delay, the beads located inside the microwells remain hydrated because of the presence of the matrix surface layer in the microarray substrate, which slows down evaporation of water from the microwells.

Example 8

Eluting Analytes from a Bead Array

A bead array containing affinity bound peptides was produced as previously described and subsequently prepared for analysis by MALDI TOF MS. The beads were placed into individual microwells of the reusable microarray substrate. Prior to placing the beads on the microarray substrate, all microwells were filled with deionized water.

The fabricated bead array was briefly centrifuged using a custom designed slide spinner at the speed of 6000 RPM to remove droplets of bulk water from the gasket surface without displacing the beads from the microwells. The bead array was then placed into the matrix sprayer and repeatedly exposed to an aerosol containing a solution of MALDI matrix, which was delivered using a custom designed spraying protocol.

The matrix solution spraying protocol was designed to adjust the rate of matrix solution deposition according to the ambient humidity level as measured by a hygrometer, such that the rate of the matrix solution deposition into the microwells is approximately equivalent to the rate at which the solvent of the matrix solution is escaping from the microwell via evaporation. For ambient humidity levels between 35% and 65% of relative humidity and indoor temperature between 20 and 28° C., the matrix deposition parameters of iMatrixSpray were set as follows: Height: 60 mm; Line Distance: 0.5 mm; Speed: 60 mm/s; Density: 5 µL/cm$^2$; Number of cycles: 10; Delay: 0 sec; Spray area width: 80 mm; Spray area depth: 30 mm. For ambient humidity levels between 15% and 35%, the speed parameter was changed to 90 mm/s, the other parameters remaining the same. For ambient humidity levels between 65% and 85%, the speed parameter was changed to 40 mm/s and the line distance parameter to 0.3 mm, the other parameters remaining the same. In all cases, the MALDI matrix solution contained 5 mg/ml of α-hydroxy cinnamic acid (CHCA), 0.4% (v/v) of TFA and 50% (v/v) of acetonitrile.

In order to prevent splattering of the liquid medium from the microwells, the pressure setting for the carrier nitrogen gas of iMatrixSpray was set to 0.09 MPa, slightly below the lowest recommended setting of 0.1 MPa.

Example 9

Distinct Shape of Microarray Spots Containing Bead-Eluted Analytes

Figure 4:
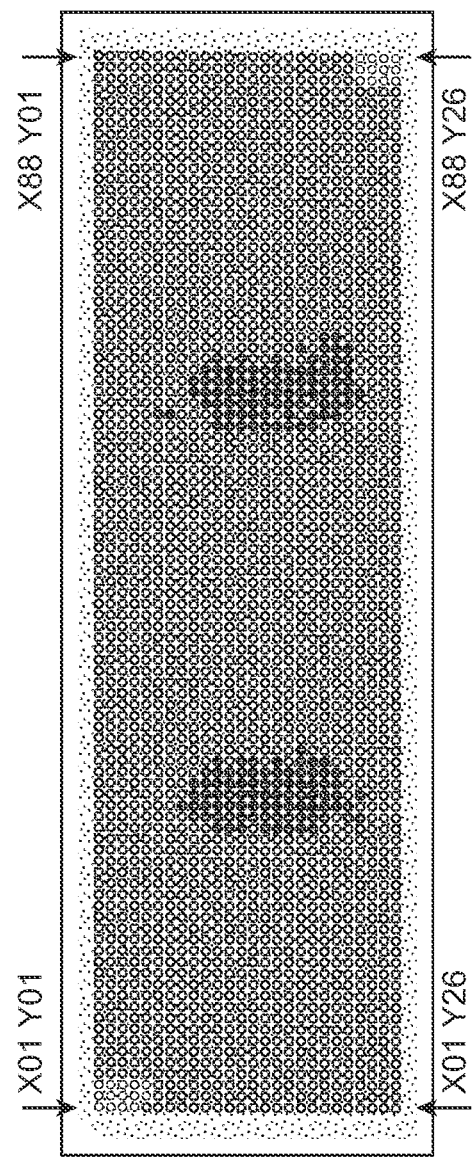
FIG. 4 is a photograph of a microarray of spots that contain MS matrix.

FIG. 4 is a photograph of a gold-coated microscope slide containing a microarray of spots produced using the previously described methods. The microarray has 88 columns, 26 rows and contains a total of 2288 spots. The fiducial is located in the upper left corner adjacent to the spot X01 Y01. Two larger irregular shape spots that cover an area of several regular spots are visible in the upper left and lower right corners of the microarray. These spots were manually added to the microarray and contain a calibration standard, namely trypsin-digested bovine serum albumin (BSA). Two regions of the microarray that contain analytes are located within columns X24-X31 and X58-X66, respectively and are identifiable by the characteristic donut or crescent shape of the spots formed in locations that previously contained a bead. No spots were detected that previously contained more than one bead. The two regions contain analytes obtained from distinct biological samples and are separated by several rows and/or columns of spots that are devoid of biological analytes, e.g. peptides. Spots that did not previously contain a bead are identifiable by their uniform pattern of matrix coverage. The analyte-devoid spots that are located within a region containing bead-eluted analytes have a different density of the matrix coverage compared to the analyte-devoid spots located in rows and/or columns that separate distinct regions. Specifically, analyte-devoid spots located in the area defined by coordinates X58-X66 and Y03-Y08 have a visibly distinct density of matrix coverage compared to adjacent spots in columns X67-X88 and rows Y1-Y2. The visually distinct appearance of such spots was also evident when the microarray was examined using a video camera of a MALDI TOF mass spectrometer (Bruker Daltonics Autoflex Speed).

The characteristic shape of microarray spots that initially contained a bead and therefore contained or were suspected of containing bead-eluted analytes was used to select such spots for MS analysis and to exclude spots that did not contain a bead and therefore were not expected to contain analytes of interest. For example, spots with coordinates X24Y11 and X24Y12 were selected for MS analysis, while spots with coordinates X24Y07 and X24Y08 were excluded from MS analysis. The process of spot selection involved optically analyzing the microarray, either manually or automatically using a photograph or a scanned image of the microarray. The selected analyte-containing spots were submitted for batch mode data acquisition using the AutoXecute mode of Autoflex Speed or analyzed individually. In either case, the MS data was acquired from an entire area of each selected spot including inner areas that contained little or no matrix.

While the microarray shown here was produced using CHCA MALDI matrix it is noted that other types of MALDI matrix including SA will produce similar visual effects to enable spot differentiation and classification.

Example 10

Optically Encoded Microarray

The pattern of analyte-containing spots within the microarray shown in FIG. 4 was used to encode the microarray, that is to unambiguously associate information about the microarray with an optical image of the microarray. The microarray contains 2288 spots with some spots having a characteristic donut or crescent shape, other spots having a round shape. All spots form a square grid. As previously noted, the donut or crescent-shaped spots contain or are suspected of containing analytes, which were captured on individual reactive sites of a bead array, while round-shaped spots are blank and not suspected of containing bead-captured analytes. Because locations of analyte-containing spots throughout the microarray are random and not identical between different microarrays, the coordinates of such spots may be used to encode the microarray. The number of possible encoding combinations is determined by the number of analyte-containing spots and is sufficient to encode thousands of microarrays.

For the exemplary microarray shown in FIG. 4, a small fraction of the total number of spots was used to create an encoding combination. The combination included X24Y11, X24Y12, X25Y09, X25Y10 as coordinates of 4 donut/crescent-shaped spots and X24Y07, X24Y08, X25Y07, X25Y08 as coordinates of 4 round-shaped spots. A total of 8 spots out of 2288 spots were used to create the encoding combination, which included both blank and analyte-containing spots. The combination was associated with an information about the microarray, namely time and date of the microarray manufacture, description of biological samples used for the microarray manufacture, description of the bead arrays used for the microarray manufacture, ID and location of a person or a robotic workstation that produced the microarray and whether the microarray has been previously measured by MS.

The described encoding method is useful for maintaining identity of microarrays as they are being transferred between the sample preparation module, e.g. MALDI matrix sprayer and the measurement module, e.g. MALDI MS instrument.

It is also useful for keeping track of microarrays as they are shipped to a different location, e.g. by mail. It is also useful for storing microarrays and subsequently retrieving them from storage for additional measurements. It is noted that the described encoding system is compatible with the sample-consuming methods of analysis because MS matrix is usually not fully depleted during a single MS analysis thereby preserving the visual appearance of individual spots and also because the spots that do not contain analytes may not need to be measured thereby also preserving their visual appearance in multiple measurements.

Overall, this Example describes methods of encoding and decoding microarrays, in which a spot that contains or is suspected of containing an analyte is visibly distinct from a spot that does not contain the analyte, the analyte-containing spot and the analyte-devoid spot having visibly distinct distribution of matrix for mass spectrometry within respective spots. The microarray encoding method includes steps of creating a decoding combination that includes coordinates of at least two spots within the microarray and associating the decoding combination with information about the microarray. In an embodiment, at least one of the at least two spots is an analyte-containing spot and at least one of the at least two spots is an analyte-devoid spot. An example of a decoding combination for the microarray in FIG. 4, which is based on coordinates of 8 spots, is X24Y11(A), X24Y12(A), X25Y09(A), X25Y10(A), X24Y07(B), X24Y08(B), X25Y07(B), X25Y08(B), where A denotes an analyte-containing (Analyte) spot and B denotes an analyte-devoid (Blank) spot. The microarray decoding method includes steps of obtaining a first microarray, obtaining a decoding combination, which contains coordinates of at least two spots within a second microarray and is associated with information about the second microarray, matching coordinates of at least two spots within the first microarray with the coordinates present in the decoding combination and verifying that the first microarray is identical to the second microarray, thereby obtaining information about the first microarray. In an embodiment, at least one of the at least two spots in the decoding combination is an analyte-containing spot and at least one of the at least two spots is an analyte-devoid spot. In an embodiment, the microarray decoding combination further includes information about localization of the matrix for mass spectrometry within an analyte-containing spot. For example, in reference to FIG. 4, it can be seen that the analyte-containing spots X24Y11 and X24Y12 have visibly distinct localization of the matrix within respective spots.

Example 11

Binding an Analyte to Distinct Reactive Sites of a Bead Array

The sample is 1 mg of Lys-C digested human brain tissue dissolved in 200 μL of the binding buffer. The bead array is assembled by individually preparing and subsequently combining 6 distinct reactive sites, each of the reactive sites containing a capture agent (antibody) that recognizes a specific epitope within the human microtubule-associated protein tau. The entry number and the entry name for tau in the Universal Protein Resource (UniProt) database are P10636 and TAU_HUMAN, respectively. Each of the 6 distinct reactive sites is provided in triplicate, therefore the bead array contains a total of 18 reactive sites. The unconjugated antibodies were purchased from Abcam (Cambridge, Mass.) and BioLegend (San Diego, Calif.). All antibodies were provided in BSA and azide-free form. The catalog numbers are Abcam 242345, BioLegend 806503, Abcam 244231, Abcam 156623, Abcam 196359 and BioLegend 806404. The procedure of antibody conjugation to the beads was performed as previously described.

The specificity of each antibody was determined using immunoaffinity capture of proteolytic fragments of tau on individual beads followed by MS and MS-MS analysis of the captured fragments.

The #242345 antibody captured multiple analytes that correspond to various proteolytic fragments of tau between amino acids 50-150 including analytes with m/z values (monoisotopic) of 2178.0 (fragment 88-109), 2773.3 (fragment 85-112), 2993.3 (fragment 91-120), 3954.8 (fragment 88-126), 4400.1 (fragment 103-145) and 4546.1 (fragment 93-136). All tau protein sites are numbered according to the canonical sequence of the isoform PNS-tau containing 758 amino acids, UniProt identifier P10636-1. It was noted that many of the detected fragments contained cleavage sites that were not specific to LysC.

The #806503 antibody captured an analyte with m/z value of 2677.2 that was assigned to the acetylated N-terminal fragment of tau containing amino acids 2 through 24.

The #244231 antibody captured an analyte with m/z value of 2391.0 that was assigned to the fragment of tau containing amino acids 45 through 67.

The #156623 antibody captured analytes with m/z values of 5599.6 and 5679.6, which were assigned to the C-terminal fragment of tau containing amino acids 703 through 755, and 2 and 3 phosphorylated sites, respectively.

The #196359 antibody captured multiple analytes with m/z values of 3533.7, 3613.6, 3693.6, 3773.6 corresponding to the fragment of tau containing amino acids 508 through 541 and 1, 2, 3 and 4 phosphorylated sites, respectively. The #196359 antibody also captured analytes with m/z values of 3661.7, 3741.7 and 33821.7 corresponding to the fragment of tau containing amino acids 508 through 542 and 1, 2 and 3 phosphorylated sites, respectively. The 508-541 fragment contains 0 missed cleavage sites for LysC while the 508-542 fragment contains 1 missed cleavage site. The #196359 antibody further captured analytes with m/z values of 2131.9, 2211.9 and 2291.8 corresponding to the fragment of tau containing amino acids 508 through 528 and 1, 2 and 3 phosphorylated sites, respectively. The 508-528 fragment contains LysC-specific cleavage site on the N-terminus (Lys) and non LysC-specific cleavage site on the C-terminus (Arg). According to the manufacturer, the #196359 antibody specifically recognizes phosphorylated Ser519 in human tau.

The #806404 antibody captured analytes with m/z values of 3453.7, 3533.7 and 3613.6, which were assigned to the fragment of tau containing amino acids 508 through 541 and 0, 1 and 2 phosphorylated sites, respectively. The #806404 antibody also captured analytes with m/z values of 3581.8 and 3661.8, which were assigned to the fragment of tau containing amino acids 508 through 542, and 0 and 1 phosphorylated sites, respectively. The 508-541 fragment contains 0 missed cleavage sites for LysC while the 508-542 fragment contains 1 missed cleavage site. The #806404 antibody also captured analytes with m/z values of 1808.8 and 1888.8, which were assigned to the fragment of tau containing amino acids 508 through 526, and 0 and 1 phosphorylated sites, respectively. The #806404 antibody also captured analytes with m/z values of 2051.9 and 2131.9, which were assigned to the fragment of tau containing amino acids 508 through 528, and 0 and 1 phosphorylated sites, respectively. The 508-526 and 508-528 fragments both contain the LysC-specific cleavage site on the N-terminus (Lys) and non LysC-specific cleavage site on the C-terminus (Arg). According to the manufacturer, the #806404 antibody specifically recognizes a fragment of human tau containing amino acids 527 through 547.

Contacting the human brain sample with the 6-plex bead array causes the singly phosphorylated 508-541 fragment of tau (m/z 3533.7) to bind to the reactive sites containing the antibody #196359 and the antibody #806404 and the 508-541 fragment of tau containing zero phosphorylation sites (m/z 3453.7) to bind only to the reactive site containing the antibody #806404.

Example 12

Incubating Bead Arrays with Different Amounts of a Sample

The first sample is 1 mg of trypsin digested MKN45 cell lysate dissolved in 200 μL of the binding buffer. The second sample is 50 μg of the trypsin digested MKN45 cell lysate dissolved in 200 μL of the binding buffer. Each of the first and second bead arrays contained 3 replicates of a reactive site that contained a capture agent for human voltage-dependent anion-selective channel protein 1 (VDAC1). The entry number and the entry name for VDAC1 in the UniProt database are P21796 and VDAC1 HUMAN, respectively. The BSA- and azide-free VDAC1 antibody was purchased from Abcam, catalog number 240128. According to the manufacturer, the immunogen for the #240128 antibody is a "synthetic peptide within Human VDAC1/Porin aa 1-100 (N terminal)".

The first sample was contacted with the first bead array and the second sample was separately contacted with the second bead array. Individual reactive sites of the first and the second bead arrays were analyzed by MS. In both the first and the second samples, the #240128 antibody captured analytes with monoisotopic m/z values of 1173.6 and 2473.1. The 1173.6 signal was assigned to the N-terminally acetylated fragment of VDAC1 containing amino acids 2 through 12. The 2473.1 signal was assigned to the N-terminally acetylated fragment of related protein VDAC2 (P45880, VDAC2 HUMAN) containing amino acids 2 through 23. VDAC1 and VDAC2 share significant sequence similarity in the N-terminal region. It was observed that the measured ratio of VDAC1 fragment to VDAC2 fragment was higher in the first sample that contained 1 mg of total input peptide compared to the second sample that contained 1/20 of the amount of total input peptide of the first sample. This Example demonstrates that competitive binding of protein fragments that are derived from different proteins, yet contain an epitope that is recognized by the corresponding antibody may be probed in the bead array format by contacting identical reactive sites with different amounts of a same sample.

Example 13

Consecutively Incubating a Sample with Multiple Bead Arrays

The sample is 1 mg of trypsin digested HCT116 human colon cancer cell lysate dissolved in 200 μL of the binding buffer. Each of the first and second bead arrays contained 3 replicates of a reactive site that contained a capture agent for eukaryotic translation initiation factor 4E-binding protein 1 (Q13541, 4EBP1_HUMAN). The BSA- and azide-free 4E-BP1 antibody was purchased from Cell Signaling Technology, catalog number 9644. According to manufacturer, "the 4E-BP1 (53H11) Rabbit mAb is produced by immunizing rabbits with a synthetic peptide corresponding to residues surrounding Ser112 of human 4E-BP1".

The sample was contacted with the first bead array as described previously. After the incubation, an unreacted portion of the sample was saved and within 24 hrs contacted with the second bead array. In a separate experiment, the sample was subjected to at least one freeze-thaw cycle after the incubation with the first bead array and before incubation with the second bead array.

Individual reactive sites of the first and the second bead arrays were analyzed by MS. In both the first and the second bead arrays, the #9644 antibody captured analytes with monoisotopic m/z values of 1468.6 and 1496.6. The 1468.6 and 1496.6 signals had nearly identical intensity. The 1468.6 signal was assigned to the C-terminal fragment of 4E-BP1 containing amino acids 106 through 118. The 1496.6 signal was assigned to the same C-terminal fragment of 4E-BP1 containing an A107V amino acid substitution that causes a +28 Da mass shift. According to the public database of somatic mutations in cancer, namely COSMIC Cell Lines Project from canSAR of Institute of Cancer Research UK, the HCT116 cell line contains a missense mutation A107V in 4E-BP1. The A107V mutation is essentially unique to HCT116 as it is not found in other commonly used cancer cell lines This Example illustrates the concept of saving an unreacted portion of a sample and using it to perform multiple sequential immunoaffinity enrichment reactions. The same target (C-terminal fragment of 4E-BP1) was enriched in two consecutive immunoaffinity reactions. The unique cell line proteomic signature, namely the two equal intensity signals separated by 28 Da was used to confirm the identity of the sample as being obtained from the HCT116 cell line. It is possible to provide a bead array containing additional capture agents that are specific for unique proteomic signatures of other cell lines. Furthermore, the quantitative nature of MS also allows monitoring of contamination of a particular cell line with a different cell line. In this Example, detecting even a trace of contamination with the HCT116 cell line is possible by monitoring the appearance of a signal near 1496.6 in a spectrum that contains the wild-type 4E-BP1 signal near 1468.6. As the dynamic range of MALDI MS instruments routinely span 3 orders of magnitude, it is possible to detect contamination of a cell line with less than 10% and even less than 1% of another cell line.

All patents, patent applications, and published references cited herein are hereby incorporated by reference in their entirety. While the present disclosure has been described in connection with the specific embodiments thereof, it will be understood that it is capable of further modification. Furthermore, this application is intended to cover any variations, uses, or adaptations of the disclosure, including such departures from the present disclosure as come within known or customary practice in the art to which the disclosure pertains, and as fall within the scope of the appended claims.

REFERENCES www.thermofisher.com/us/en/home/life-science/protein-biology/protein-biology-learning-center/protein-biology-resource-library/protein-biology-application-notes/calculate-number-immobilized-proteins-per-bead-agarose-affinity-supports.html ThermoFisher Scientific Application Note: A consideration of relative sizes and dimensions of agarose resin beads, antibodies, proteins, chemical modification groups, and affinity ligands by Douglas A. Hayworth, Ph.D.; Greg T. Hermanson, B.S. dated Mar. 3, 2014, website accessed Jul. 4, 2019

What is claimed is:

1. An analytical method, the method comprising the steps of contacting a sample with a bead array, the sample containing a first peptide and a second peptide, the bead array containing a first reactive site, the first reactive site comprising a bead, a capture agent associated with the bead that specifically recognizes the first peptide, and a distinct capture agent associated with the bead that specifically recognizes the second peptide, wherein a binding capacity of the bead array is greater than an amount of the first peptide and lower than an amount of the second peptide in the sample,
   measuring a ratio of the first peptide to the second peptide in the first reactive site using mass spectrometry, and using a ratio to determine the amount of the first peptide in the sample,
   wherein the ratio of the first peptide-specific capture agent to the second peptide-specific capture agent in the first reactive site is greater than 5:1.

2. The method of claim 1 wherein the contacting step causes more than 50% of the amount of the first peptide and less than 50% of the amount of the second peptide to bind to the bead array.

3. The method of claim 1 wherein the second peptide is synthetic.

4. The method of claim 1 wherein the second peptide is a proteolytic fragment of a naturally occurring protein.

5. The method of claim 1 further comprising the step of obtaining an estimate of a total protein content of the sample before the contacting step.

6. The method of claim 1 wherein one of the first peptide and the second peptide contains a post-translational modification (PTM).

7. The method of claim 1 wherein the first peptide contains an amino acid sequence that naturally occurs in at least 2 distinct proteins, the at least 2 distinct proteins being constituents of distinct biological pathways.

8. The method of claim 1 wherein the capture agent specific for the first peptide further specifically recognizes a third peptide and wherein the binding capacity of the bead array is greater than a combined amount of the first and the third peptides in the sample.

9. The method of claim 8 wherein the first and the third peptides are derived from a common precursor protein.

10. The method of claim 8 wherein one of the first and the third peptides contains a PTM.

11. The method of claim 1 wherein the capture agent specific for the second peptide further specifically recognizes a third peptide and an amount of the third peptide in the sample is less than 10% of the amount of the second peptide.

12. The method of claim 1 wherein the bead array further contains a second reactive site, the second reactive site comprising a bead, a capture agent that specifically recognizes a peptide that is distinct from the first peptide, and the capture agent specific for the second peptide.

13. The method of claim 1 further including the step of using a molecular weight of the second peptide or an equivalent thereof to calibrate a mass spectrum that contains signals from the first and the second peptides.

14. The method of claim 1 wherein the first peptide is a fragment of protein TAU.

15. An analytical method, the method comprising the steps of contacting a sample with a bead array, the sample containing a first peptide and a second peptide, the bead array containing a first reactive site and a second reactive site, each of the first and the second reactive sites comprising a bead and a capture agent, the capture agent of the first reactive site specifically recognizing the first peptide and the second peptide, the capture agent of the second reactive site specifically recognizing the first peptide and not the second peptide, wherein a binding capacity of the bead array is greater than, equal to, or lower than an amount of the first peptide in the sample, measuring a ratio of the first peptide to the second peptide in the first reactive site using mass spectrometry, and using the ratio to quantitatively determine the amount of the first peptide in the sample, wherein the sample after the contacting step contains the first peptide and the second peptide.

16. The method of claim 15 wherein the first and the second peptides are fragments of protein TAU.

17. An analytical method, the method comprising the steps of contacting a first sample with a first bead array, contacting a second sample with a second bead array, each of the first and the second samples containing a first peptide and a second peptide, each of the first and the second bead arrays containing a reactive site that comprises a bead and a capture agent that specifically recognizes the first peptide and the second peptide, wherein a binding capacity of the first bead array is greater than a combined amount of the first and the second peptides in the first sample and a binding capacity of the second bead array is lower than a combined amount of the first and the second peptides in the second sample, measuring a ratio of the first peptide to the second peptide in the reactive site of the first bead array using mass spectrometry, measuring a ratio of the first peptide to the second peptide in the reactive site of the second bead array using mass spectrometry, and using the ratio to determine the amount of the first peptide in the first sample.

18. An analytical method, the method comprising the steps of contacting a sample with a first bead array, the sample containing a first peptide and a second peptide, the first bead array containing a reactive site that comprises a bead and a capture agent that specifically recognizes the first peptide and the second peptide, wherein a binding capacity of the first bead array is greater than, equal to, or lower than a combined amount of the first and the second peptides in the sample, then, contacting the sample with a second bead array, the second bead array containing a reactive site that comprises a bead and the capture agent, measuring a ratio of the first peptide to the second peptide in the reactive site of the second bead array using mass spectrometry, and using the ratio to determine the amount of the first peptide in the sample.

19. The method of claim 18 wherein the sample is subjected to at least one freeze-thaw cycle between the two contacting steps.

\* \* \* \* \*

```
                       SEQUENCE LISTING

<160> NUMBER OF SEQ ID NOS: 5

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: phosphoThr

<400> SEQUENCE: 1

Val Ala Asp Pro Asp His Asp His Thr Gly Phe Leu Thr Glu Tyr Val
1               5                   10                  15

Ala Thr Arg

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: phosphoThr
<220> FEATURE:
<221> NAME/KEY: MOD_RES
<222> LOCATION: (15)..(15)
<223> OTHER INFORMATION: phosphoTyr

<400> SEQUENCE: 2

Val Ala Asp Pro Asp His Asp His Thr Gly Phe Leu Thr Glu Tyr Val
1               5                   10                  15

Ala Thr Arg

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: phosphoThr

<400> SEQUENCE: 3

Ile Ala Asp Pro Glu His Asp His Thr Gly Phe Leu Thr Glu Tyr Val
1               5                   10                  15

Ala Thr Arg

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (13)..(13)
<223> OTHER INFORMATION: phosphoThr
<220> FEATURE:
<221> NAME/KEY: MOD_RES
<222> LOCATION: (15)..(15)
<223> OTHER INFORMATION: phosphoTyr

<400> SEQUENCE: 4

Ile Ala Asp Pro Glu His Asp His Thr Gly Phe Leu Thr Glu Tyr Val
1               5                   10                  15

Ala Thr Arg

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: phosphoThr

<400> SEQUENCE: 5

Gly Ser Pro Ser Gly Leu Arg Pro Arg Gly Tyr Thr Ile Ser Asp Ser
1               5                   10                  15

Ala Pro Ser Arg
            20
```